United States Patent
Clark et al.

(10) Patent No.: US 6,171,112 B1
(45) Date of Patent: Jan. 9, 2001

(54) METHODS AND APPARATUS FOR AUTHENTICATING INFORMED CONSENT

(75) Inventors: Robert L. Clark, Bellevue; Glen A. Morgan, Kent, both of WA (US)

(73) Assignee: Wyngate, Inc., Bellevue, WA (US)

(*) Notice: Under 35 U.S.C. 154(b), the term of this patent shall be extended for 0 days.

(21) Appl. No.: 09/328,685

(22) Filed: Jun. 9, 1999

Related U.S. Application Data

(63) Continuation-in-part of application No. 09/156,460, filed on Sep. 18, 1998.
(60) Provisional application No. 60/137,364, filed on Jun. 3, 1999.

(51) Int. Cl.$^7$ .................................................. G09B 7/00
(52) U.S. Cl. ..................... 434/322; 434/362; 434/321; 705/2
(58) Field of Search .................................. 434/219, 262, 434/354, 321, 322, 362, 350, 307 R; 705/2, 3

(56) References Cited

U.S. PATENT DOCUMENTS

| | | |
|---|---|---|
| 3,273,260 | 9/1966 | Walker . |
| 3,481,052 | 12/1969 | Dorsett . |
| 3,504,445 | 4/1970 | Goldmark et al. . |
| 3,566,370 | 2/1971 | Worthington, Jr. et al. . |
| 3,794,982 | 2/1974 | McCormick et al. . |
| 3,839,708 | 10/1974 | Bredesen et al. . |
| 3,939,579 | 2/1976 | Andrews et al. . |
| 3,946,503 | 3/1976 | Buchan et al. . |
| 3,968,576 | 7/1976 | Taylor . |
| 3,970,996 | 7/1976 | Yasaka et al. . |
| 4,053,951 | 10/1977 | Hudspeth et al. . |
| 4,085,446 | 4/1978 | Nagamura . |
| 4,130,881 | 12/1978 | Haessler et al. . |

(List continued on next page.)

FOREIGN PATENT DOCUMENTS

| | | | |
|---|---|---|---|
| 0 320 749 | 6/1989 | (EP) | ................................ G06F/15/42 |
| WO 93/23836 | 11/1993 | (WO) . | |

OTHER PUBLICATIONS

Strickland et al.; "Developing a CAI Graphics Sumulation Model: Guidelines"; *T H E Journal*; V 16 N 7; 88(5); Mar. 1989 Dialog: File275, Acct# 01293856.

(List continued on next page.)

*Primary Examiner*—Valencia Martin-Wallace
*Assistant Examiner*—Chanda Harris
(74) *Attorney, Agent, or Firm*—Wilson Sonsini Goodrich & Rosati

(57) ABSTRACT

A method and apparatus for recorded information conveyance and comprehension are provided that include a Virtual Interactive Teaching and Learning (VITAL) Center. The VITAL Center provides an interactive patient education and informed consent process that increases patient comprehension using presentations that offer a baseline education about medical and surgical procedures including the associated risks, benefits and alternatives. The patient's comprehension of the material is confirmed throughout the presentation using summary questions focused on key information. The patient is able to record their own questions or concerns about the procedure while watching the presentation. After the presentation is finished, A healthcare professional reviews the patient questions upon completion of the presentation, and any information the patient did not understand is further explained at this time. After all questions and concerns are addressed and the patient has a comfortable understanding of the procedure, the patient signs an informed consent electronically. Using digital video capture, the VITAL Center simultaneously records the information presented, the patient viewing the interactive presentation, the patient-physician interaction, and the informed consent process. The entire recorded education session and informed consent is stored permanently on optical disk media.

43 Claims, 28 Drawing Sheets

U.S. PATENT DOCUMENTS

| | | |
|---|---|---|
| 4,205,387 | 5/1980 | Ovshinsky et al. . |
| 4,228,506 | 10/1980 | Ripley et al. . |
| 4,260,854 | 4/1981 | Kolodny et al. . |
| 4,346,449 | 8/1982 | Ovshinsky et al. . |
| 4,359,223 | 11/1982 | Baer et al. . |
| 4,360,345 | 11/1982 | Hon . |
| 4,395,236 | 7/1983 | Gotthold . |
| 4,459,114 | 7/1984 | Barwick . |
| 4,475,132 | 10/1984 | Rodesch . |
| 4,482,328 | 11/1984 | Ferguson et al. . |
| 4,518,267 | 5/1985 | Hepp . |
| 4,552,535 | 11/1985 | Steffel . |
| 4,569,421 | 2/1986 | Sandstedt . |
| 4,593,904 | 6/1986 | Graves . |
| 4,602,907 | 7/1986 | Foster . |
| 4,611,298 | 9/1986 | Schuldt . |
| 4,671,772 | 6/1987 | Slade et al. . |
| 4,685,122 | 8/1987 | Deveson et al. . |
| 4,771,344 | 9/1988 | Fallacaro et al. . |
| 4,812,125 | 3/1989 | Strashun . |
| 4,828,500 | 5/1989 | Seidel et al. . |
| 4,828,501 | 5/1989 | Ingenito et al. . |
| 4,839,743 | 6/1989 | Best et al. . |
| 4,846,693 | 7/1989 | Baer . |
| 4,863,384 | 9/1989 | Slade . |
| 4,893,270 | 1/1990 | Beck et al. . |
| 4,895,376 | 1/1990 | Shiung-Fei . |
| 4,907,146 | 3/1990 | Caporali . |
| 4,907,973 | 3/1990 | Hon . |
| 4,930,019 | 5/1990 | Chu . |
| 4,931,018 | 6/1990 | Herbst et al. . |
| 4,937,743 | 6/1990 | Rassman et al. . |
| 4,948,371 | 8/1990 | Hall . |
| 4,959,734 | 9/1990 | Foster . |
| 5,002,491 | 3/1991 | Abrahamson et al. . |
| 5,006,987 | 4/1991 | Harless . |
| 5,025,374 | 6/1991 | Roizen et al. . |
| 5,033,969 | 7/1991 | Kamimura . |
| 5,035,625 | 7/1991 | Munson et al. . |
| 5,059,127 | 10/1991 | Lewis et al. . |
| 5,065,315 | 11/1991 | Garcia . |
| 5,146,439 | 9/1992 | Jachmann et al. . |
| 5,167,506 | 12/1992 | Kilis et al. ............................. 434/262 |
| 5,276,775 | 1/1994 | Meng ..................................... 395/55 |
| 5,289,531 | 2/1994 | Levine ................................... 379/93 |
| 5,303,042 | 4/1994 | Lewis et al. . |
| 5,321,605 | 6/1994 | Chapman et al. .................... 364/402 |
| 5,398,336 | 3/1995 | Tantry et al. ......................... 395/600 |
| 5,553,609 | 9/1996 | Chen et al. ............................ 128/630 |
| 5,654,750 | 8/1997 | Weil et al. . |
| 5,799,282 | 8/1998 | Rakshit et al. ............................ 705/2 |
| 5,802,494 | * 12/1998 | Kuno ..................................... 705/2 X |
| 5,823,948 | 10/1998 | Ross, Jr. et al. ....................... 600/300 |
| 5,842,173 | 11/1998 | Strum et al. ............................. 705/1 |
| 5,848,901 | * 12/1998 | Kim et al. ........................ 434/362 X |
| 5,999,909 | * 12/1999 | Rakshit et al. ....................... 705/2 X |
| 6,014,630 | * 1/2000 | Jeacock ................................ 705/3 X |
| 6,064,968 | * 5/2000 | Schanz ................................. 705/1 X |

OTHER PUBLICATIONS

Davis et al.; "The Gap Between Patient Reading Comprehension and the Readability of Patient Education Materials"; *Journal of Family Practice*; V 31 N 5; pp. 533(6); Nov. 1990; Dialog: File 149, Acct# 9213052.

Dialog Abstract; Kearsley et al.; "Microcomputer–based Training in Business and Industry: Present Status and Future Prospects"; *Journal of Education Technology Systems*; v10 n2; pp. 101–108; 1981–1982; Dialog File 2, Acct# 01860303.

Dialog Abstract; Gayeski; "Interactive Video: Integrating Design Levels and Hardware Level"; *Journal of Educational Technology Systems*; v 13 n 3; pp. 145–151; 184–185; Dialog: File 2 Acct# 02475642.

Goldes; "Acronyms For Education" *PC Magazine*; v 3 n7; pp. 353–355; Apr. 17, 1984; Dialog: File 148 Acct# 02057293.

Videos, Questionnaires Aim to Expand Role of Patients in Treatment Decisions; R. Winslow; Wall Street Journal; Feb. 1992; B1, B.

FPR Offers computer–Generated Patient Education Aid Program; Family Practice Recertification; B. MacKenion Feb. 1992; pp. 17.

Tips from other Journals; American Family Physician; Feb. 1992 pp. 829.

Infor. Seeking & Interactive Videodisc Preperation For Third Molar Extracton; Journal of Oral Maxillofacial Surgery; D. Ader; 1991; pp. 27–32.

CBT Options–Solutions & Systems; Civil Aviation Training; T. Nash; pp. 38–43.

Big is Beautiful–Pilot Training at American Airlines; Civil Aviation Training; D. Saw; 1991; pp. 4–6.

Military Training Programs; Military Standard; U. S. Government Department of Defense; Dec. 1990; pp. 1, 65–73.

Surgical Informed Consent: What it is and is Not; American Journal of Surgery; W. Sterling Edwards; Apr. 1987; pp. 574–578.

Advanced Aircrew Training System (AATS); Function Design Description; Seville Technical Document TD 87–12; K.R. Williams, et al.; Oct. 1987.

Smith; "How to Design Interactive Training Programs"; *Training*; v 20 n12; pp. 30–45; Dec. 1983.

D. Taylor; "Object–Oriented Technology"; *A Managers Guide*; Addison–Wesley Publishing Company; 1990.

Patient Consent Form; Approved by the Colorado Medical Society Risk Management Committe.

Informed Consent? Plastic Surgeons Had Warnings on Safety of Silicone Implants; J. Rigdon; Wall Street Journal Mar. 12, 1982; A1,A8.

Doctors Turns to Software to Avoid Malpractice Suits; G. Ruffenach; Wall Street Journal; App. Mar. 2, 1992.

Training–Instructional System Development; Air Force Manual 50–2 U.S. Government–Dept. of Air Force; Jul. 1986; pp. 23–31.

Chapter 30 Consents; Operating Room Admin. Manual; Various Contributors; Approx. 1990; 30: 1–30:26.

An Approach to the Evaluation of Tailored Testing; Research Report; KathleenDaubek, et al.; Dec. 1973; pp. 1–12.

Barbour et al., "Videotape Aids Informed Consent Decision", Journal of the American Medical Association, Dec. 15, 1978, vol. 240, No. 25.

Hume, Gregory D., "A Dynamic Student Model In a Cardiovascular Intelligent Tutoring System", Fifth Annual IEEE Symposium on Computer–Based Medical Systems, Jun. 14–17, 1992.

Webber, W. et al., "Computer–Based Multimedia In Plastic Surgery Education", Sixteen Annual Symposium on Computer Applications in Medical Care, Baltimore, MD, Nov. 1992, pp. 829–830.

\* cited by examiner

Patient Information

Name: john — 1711
Date of Birth: December 12, 1995 — 1712
SSN: 555-55-5555 — 1713
Medical Number: #555-55555-55

1710

1700

1799 Patient
Physician

Patient Has — 1720

Medications — 1730

Additional People — 1740

Does Not Have
Diabetic
Kidney Disease — 1750

Procedures — 1760
Cardiac Catheterization, by Michael Whiton, MD — 1761

Verification
By pressing Agree, John is verifying that all
information is complete and correct. Otherwise,
press Disagree

1770

✓ AGREE — 1771

✗ DISAGREE — 1772

FIG. 17

By signing this consent, I verify that I understand the proposed procedure, its benefits, and the options to the procedure and all of the potential complications. I understand that the physician will perform the procedure along with the delegates and assistants he requires. I agree to follow his instructions and suggestions before and following the procedure. I have been allowed time to ask any and all of the questions I have, and I have no further questions at this time. If I change my mind about this procedure, or have further questions or concern, I will discuss them fully and completely with the physician prior to the procedure.

I allow the physicians performing my procedure to use his of her judgment at the time of the procedure to perform further procedures felt to be medically necessary and appropriate. I understand and agree that each individual's body is different and no guarantee can be made concerning any risk or outcome.

Pleas use attached pen to sign on the attached pad to acknowledge your consent.

Please sign now using the signature pad.

◉ CLEAR

◇ DONE

✕ Not Ready to Sign

FIG. 24

METHODS AND APPARATUS FOR AUTHENTICATING INFORMED CONSENT

RELATED APPLICATIONS

This application is a continuation-in-part of U.S. patent application Ser. No. 09/156,460, entitled "Methods and Apparatus for Authenticating Informed Consent," filed Sep. 18, 1998 for inventors Robert L. Clark and Glen A. Morgan. This application claims priority to U.S. Provisional Patent Application serial No. 60/137,364, entitled "Methods and Apparatus for Recorded Information Conveyance and Comprehension," filed Jun. 3, 1999 for inventors Robert L. Clark and Glen A. Morgan.

FIELD OF THE INVENTION

The present invention relates generally to presenting information and, more particularly, to presenting selected information to individuals and authenticating receipt and comprehension of the information by the individuals.

BACKGROUND

Daily human interaction requires the exchange of ideas, language, symbols, data, messages, or other communications. In some situations, legal consequences arise if information is not communicated effectively. Examples of information which, if miscommunicated or not fully appreciated by the recipient can give rise to legal ramifications, are numerous. Such examples include, but are not limited to, patient information regarding the risks associated with medical procedures, and patient information regarding the use and potential side effects of medicinal drugs. Further examples include information relating to the risks associated with certain leisure or sporting activities (e.g., horseback riding, hang gliding, bungee jumping, parachuting, etc.), and information relating to the use of motor vehicles, machinery, and equipment. Moreover, another example includes any information that potentially affects the legal rights of the recipient (e.g., legal effects of taking breathalyzer tests, legal effects associated with acknowledging receipt and understanding of Miranda warnings, legal effects of accepting a plea bargain in the context of criminal litigation or a settlement offer in the context of civil litigation).

Regarding informed consent in medical procedures, the principle of informed consent is endorsed by the American College of Surgeons. The Statement ofPrinciples of the College says, in part: "Patients should understand the indications for the operation, the risks involved and the result that it is hoped to attain." Further, the College states that doctors should be willing to take whatever time is necessary to make sure the patient is fully informed and should not guarantee outcomes due to the individual differences of each patient. Research shows that the patient's unmet expectation of the outcome of surgical treatment is one of the most cited reasons for medical malpractice litigation in the United States today. Medical informed consent law requires disclosure of the risk of and alternative to suggested medical procedures to enable patients to make knowledgeable decisions about the course of their medical care. United States courts almost unanimously treat lack of informed consent as a matter of negligence on the part of the physician to disclose necessary information to patients.

The U.S. medical malpractice litigation crisis is well documented. Medical malpractice tort costs have increased 48.5% between 1990 and 1995, almost triple the 16.6% increase in overall tort costs during the same period (Tillinghast-Towers Perrin 1995, "Tort Cost Trends; An International Perspective"). According to the American Medical Association, nearly 40% of all physicians are sued at least once during their careers. The American Medical News published a report stating that medical malpractice awards have increased from an average of $1.214 million in years 1985–1989 to $1.906 million in years 1990–1995.

A close look at how informed consent is currently being given is revealing. It is not uncommon for a patient to be asked to consent to a medical or surgical procedure for diagnostic or curative purposes on the initial visit to a physician. During a 15 to 20 minute office visit, the patient must decide whether to trust the physician's expertise and follow the proposed treatment recommendations. It is up to the physician to educate the patient regarding the necessity of the procedure and its risk and benefits. However, the information presented is variable and often inconsistent. While educational material is available in a variety of media including paper, video, audio and digital files, it is not always up to date and easily accessible. Patients give their consent solely on what the physician tells them or on their understanding of the educational material they receive from the physician during the office visit.

Typically, written consent forms are used by those conveying information to a recipient in an attempt to insulate the information provider from claims that the information was not provided or was not provided effectively. Such written consent forms either contain the information itself or are executed by the recipient after oral communication of the information to the recipient by the information provider. These written consent forms generally state that execution of the consent form evidences receipt and understanding by the recipient of the information conveyed, as well as consent to the risks as described in the consent form or the associated information conveyed to the recipient.

However, consent forms alone are not necessarily the best solution to the problem of informed consent. A signed consent form does not necessarily provide insight into the state of mind, comprehension, or capacity of the recipient. For example, there may be no indication of fraud, fatigue, misunderstanding, lapse of attention, coercion or other relevant factors that prevent the recipient from fully understanding the nature of the information conveyed, arguably rendering any such consent ineffective. If the consent is ineffective, the recipient could suffer physical, legal, pecuniary or other injury which was not contemplated by the recipient. The recipient might attempt to hold the information provider liable for such injury, for, among other grounds, failure to effectively communicate the necessary information to the recipient. Therefore, uncertainty over whether the information was effectively communicated to and understood by the recipient could expose the information provider to liability despite the existence of a signed consent form.

Attempts have been made to provide information to a recipient and to test the understanding of the information using audiovisual equipment as opposed to, or in addition to, the written consent form. The following United States Patent Nos. disclose audiovisual instruction devices that may be used for informed consent: U.S. Pat. Nos. 3,273,260; 3,939,579; 3,504,445; 4,482,328; 4,552,535; 3,481,052; 3,968,576; and, 3,946,503.

U.S. Pat. No. 3,946,503 to Buchan et al. discloses a device that presents a pre-formatted audiovisual presentation to educate medical patients or other individuals on a subject. The visual portion of the presentation comprises a filmstrip and is displayed on an illuminated screen. The audio portion includes a synchronized audio tape. The Buchan device also discloses obtaining a patient's or individual's responses or answers to test questions in a condensed electrically coded form on a tape cassette. More particularly, by recording a series of tones on the cassette tape, the Buchan apparatus is able to link the questions with the answers. To retrieve the individual's responses, the audiotape is replayed whereupon the participant's responses are displayed using illuminated lights. The Buchan apparatus also provides for bypassing a series of subordinate or branching sequences of questions in response to the selection of a predetermined answer to a primary question. The Buchan apparatus is adapted to record its data in condensed form and transmit that data by a data phone set to a remotely located computer which is programmed to process the data.

The Buchan device, however, has several limitations. The Buchan device provides no visual or other authentication, like an electronic signature or retinal scan, for use in conclusively establishing that a particular individual actually engaged in the learning session. Nor does the Buchan device provide an indication of the questioning environment, such as the degree of privacy or opportunities for fraud and coercion. Also, the Buchan device fails to record the response or reaction of the recipient to the information presented along with the simultaneous presentation of the information. Thus, while generally adequate for displaying information to a person, the typical audiovisual device may not provide sufficient evidence of receipt of the information and/or the demeanor, comprehension, or overall mental and physical state of the recipient in order to adequately prove that a particular individual received certain information and was capable of understanding and fully appreciating the information conveyed.

Over the past decade, pressure has increased for healthcare providers and hospitals to contain healthcare costs while maintaining high quality care. This pressure has affected the patient-physician relationship, as it necessitates physicians to accomplish more with each patient in less time. Simply put, cost containment requires more efficient delivery of care, and too often at the expense of the patient-physician relationship. The growing regulations and administrative burdens placed on healthcare providers has additionally accelerated the need for technology-based solutions. Consequently, there is a need to enhance the quality of the patient-physician experience prior to invasive medical procedures using a method and apparatus for presenting information to a recipient while establishing receipt and comprehension of the information. There is also a need for the simultaneous provision of a correlated record of the information along with the responses. The correlated record should be capable of being archived, stored, retrieved and observed for later use. It would be particularly advantageous if the correlated record could be permanently, confidentially, and compactly stored.

SUMMARY OF THE INVENTION

A Virtual Interactive Teaching and Learning (VITAL) Center of an embodiment provides an interactive patient education and informed consent process that reduces patient anxiety, increases patient comprehension and improves the level of personal interaction between patient and physician. The VITAL Center facilitates patient understanding of recommended procedures and reduces patient anxiety using presentations that offer information that has been physician peer reviewed as well as examined by leaders in patient education and legal experts to ensure that it is accurate, current, and comprehensive. The VITAL Center, while not replacing the interaction between a patient and physician, enhances this relationship by establishing a foundation of knowledge that fosters a more meaningful patient-physician discussion about a medical or surgical procedure.

During an interactive presentation a patient watches and interacts with the VITAL Center presentation on a recommended procedure. The presentation offers a baseline education about the procedure including the associated risks, benefits and alternatives. The patient's comprehension of the material is confirmed throughout the presentation using summary questions focused on key information. The patient is encouraged to record their own questions or concerns about the procedure while watching the presentation. After the presentation is finished, a healthcare professional reviews the patient's questions or concerns, as recorded by the VITAL Center. Any information the patient did not understand is further explained at this time. After all questions and concerns have been addressed and the patient has a comfortable understanding of the procedure, the patient is asked to sign an informed consent electronically. An acknowledgment of obtaining the informed consent will be printed from the VITAL Center to be included in the patient's file. Through digital video capture, the VITAL Center simultaneously records the information presented, the patient viewing the interactive presentation, the patient-physician interaction, and the informed consent process. The entire recorded education session and informed consent is stored permanently on optical disk media. The stored sessions are archived and correlated.

An embodiment provides a method for obtaining informed patient consent. Interactive presentations are received by the VITAL Center via transmissions from a central data facility. Updated presentation material is also received from the central data facility. An interactive presentation is selected for a patient to view by a representative of a healthcare provider. The selected interactive presentation is presented to the patient. The interactive presentation may include text, audio, animations, and video presentations. During the interactive presentation, the VITAL Center records patient responses to summary questions, patient inquiries including questions, visual images of the patient observing the interactive presentation, and patient personal markers including biological markers. The patient's comprehension of the presentation is determined, and an informed patient consent is recorded if it is determined that the patient comprehends the material presented during the interactive presentation. A recorded patient education session is encrypted and transmitted by the VITAL Center to the central data facility, the patient education session including the interactive presentation, the recorded visual images of the patient observing the presentation, the recorded patient responses, the patient inquiries, and recorded personal markers. The received patient education sessions are stored and archived at the central data facility.

The descriptions provided herein are exemplary and explanatory and are intended to provide examples of the claimed invention.

BRIEF DESCRIPTION OF THE DRAWINGS

The accompanying drawings illustrate embodiments of the invention. In the drawings:

FIG. 17 is a patient verification screen of a VITAL Center of an embodiment.

FIG. 24 is an Informed Consent signature screen of a VITAL Center of an embodiment.

DETAILED DESCRIPTION

The present invention relates generally to a method and apparatus for presenting selected information to one or more individuals, and authenticating both the individual's receipt and comprehension of the information. The present invention is particularly well-suited to providing an individual with information concerning risks associated with a particular activity and authenticating the receipt and comprehension of the information by the individual as well as an informed consent to assume such risks when participating in such activity.

Figure 1:
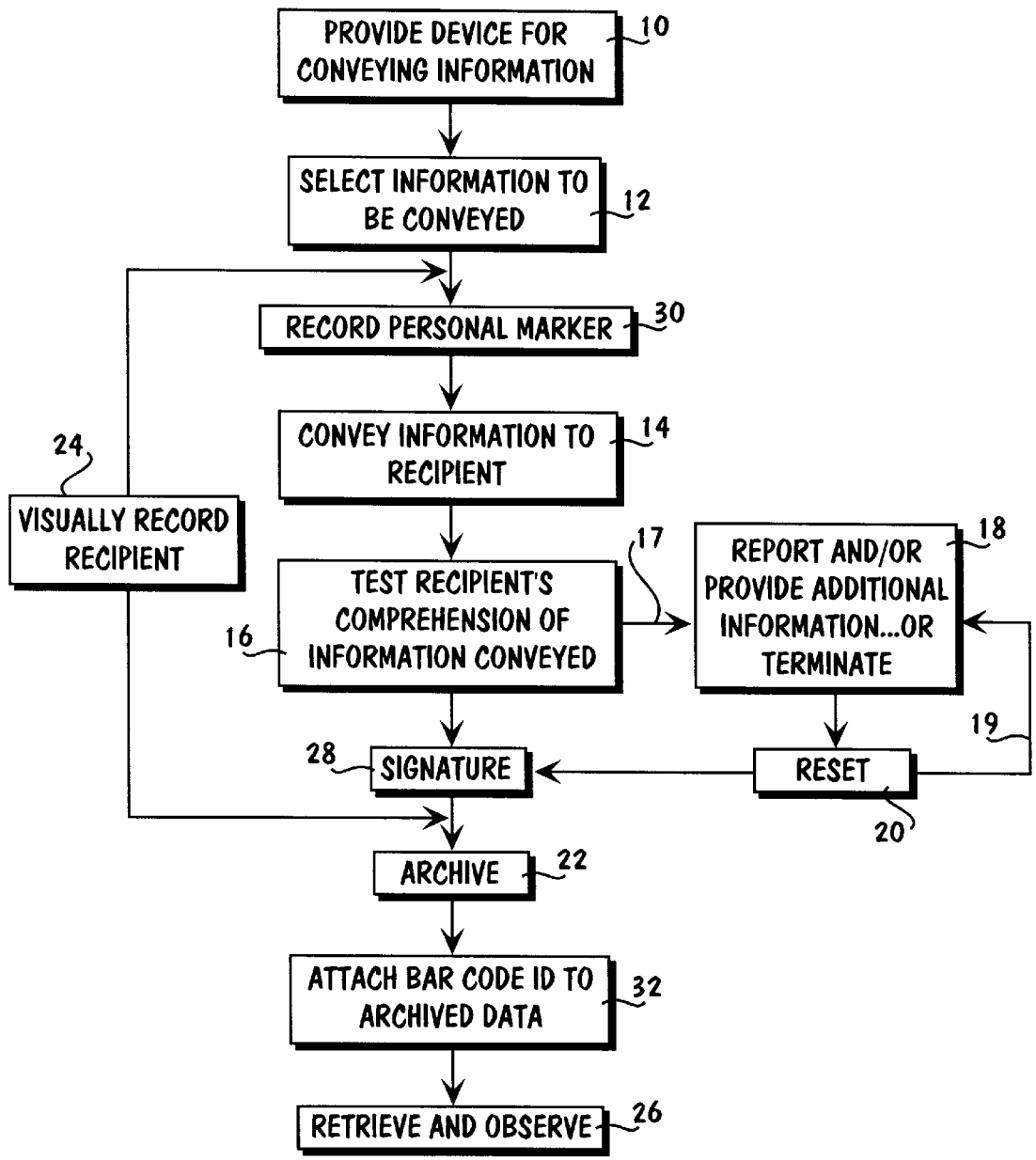
FIG. 1 is a flow diagram of a method for authenticating receipt and comprehension of information by a recipient in an embodiment.

FIG. 1 is a flow diagram of a method for authenticating receipt and comprehension of information by a recipient in an embodiment. Operation begins at block 10, at which a device is provided for conveying information to a recipient. The device may include any means for providing information to a recipient, including but not limited to audio devices, visual devices, or preferably, audiovisual devices. The device of an embodiment includes a means for permitting the recipient to input information, such as responses to questions testing the recipient's knowledge of the information provided. The device may limit the recipient's interaction to that of providing permitted responses to specific questions so as to prevent the recipient from intentionally or inadvertently corrupting the integrity of the system.

Information is selected, at block 12, for conveyance to the recipient. The information is selected by the entity seeking an informed consent from the recipient. The information is selected, at least in part, based upon the activity in which the recipient will be engaged. For example, the interactive presentation system may contain information regarding a number of activities (e.g., a number of different medical procedures, a number of different prescription medications, a number of sporting activities, a number of pieces of equipment, a number of motor vehicles). The entity or individual seeking informed consent will select the appropriate information relevant to the activity in which the recipient will be engaged which requires authentication of the recipient's informed consent.

The information is conveyed to the recipient, at block 14. The information may be provided using a simple narrative format, requiring no input from the recipient, or using an interactive system. As used herein, the term "interactive presentation system" refers to a system designed to present information to the participant and then prompt the participant with test questions regarding the information. The participant views and listens to the presented information through a display means, preferably an audio-video monitor. A test of the recipient's comprehension of the presented information is performed, at block 16. As the participant's interaction with the system may be limited due to security and data integrity concerns, the participant should indicate responses by touching a pressure-sensitive or heat-sensitive screen (e.g., a touch screen). However, in instances where a touch screen is impractical or impossible to use, responses may be inputted using a computer mouse, a keyboard, a voice recognition system, built-in display buttons, or other interactive means.

If the participant's responses indicate that the participant has insufficient comprehension of the information provided, the interactive presentation system may repeat all or selected portions of the information previously presented, present new information, terminate the learning session, or any combination thereof, at block 18. For example, if the participant fails to obtain a predetermined score on a particular aspect of the presentation, a more detailed presentation of this aspect may be provided and the participant may then be re-tested, at block 20. If the retest again indicates that participant has obtained insufficient comprehension, operation continues at block 18. If the initial testing or retesting indicates that participant has obtained a required or desired level of comprehension or is unable to do so, the participant may be provided with additional information regarding the same or different subject matter (not shown), or operation may continue with the optional signature, at block 28, or operation may continue with archiving, at block 22.

Where the information is presented in text form, the text may be written on an elementary school, for example, fifth grade, reading level to ensure comprehension across a broad section of the general population. Moreover, an option may be included to allow the participant to select interactive presentation text in a language the participant comprehends or, alternatively, which is subtitled and/or voice-over subtitled in a language the participant comprehends. The information presented may be uniquely created for each individual participant by the entity seeking the participant's informed consent, and may even include, where it is audiovisual in nature, presentations given by the entity, or its agents, seeking the authentication of informed consent. In the alternative, where standardization of the information provided is important, the provided information may include only standardized information which is provided with little or no modification to participants. In yet another embodiment of the present invention, the information provided may include both standardized information and information uniquely tailored to an individual participant.

The interactive presentation system may be audio, visual, or an audiovisual combination, preferably generated by means of a computer, but other methods of conveying information, such as real-time closed circuit or pre-recorded digital imaging may be used. Moreover, hand-held or portable devices are also envisioned, with or without the accompanying video.

Operation continues at block 24, at which the participant's interactions with the information provided, in particular where the information is provided via an interactive presentation, are simultaneously recorded in real time via a visual recording means. The visual recording means is produces a data type capable of being archived in a correlated fashion described herein. Suitable cameras include video or still cameras. The camera may operate with traditional forms of developed film or it may be a digital camera. The camera may simultaneously audibly record the participant. Moreover, in cases where a mobile interactive presentation-generating device is contemplated, fixed visual cameras can be replaced with mobile cameras. As such, the visual recording equipment provides a visual record of the participant's interaction with the interactive presentation system. The visual record may be archived on a storage medium in a correlated fashion along with the information provided and the participant's responses to the testing conducted by the interactive presentation system.

The visual recording equipment of an embodiment contains tamper-resistant features, as, for example, complete enclosure in a protected structure. Preferably, the visual recording equipment is also provided with a real-time clock and/or day/date function to record the date and/or time of the participant's interaction with the interactive presentation system. As may be appreciated, the visual recording equipment may be fitted with standard safety measures known in the art, including but not limited to low-light warning indicators and power failure warning indicators.

An additional record may be made of other measurable biological functions or parameters of the participant to supplement the visual record, including but not limited to recordation of pulse rates, breath rates, blood pressure, and nervous impulses/signals. Such other biological parameters may be measured in order to provide confirmation of the participant's physical state during the participant's interaction with the interactive presentation system. Another purpose for the biological parameters may be to provide irrefutable proof of the participant's participation with the interactive presentation where the biological parameter is unique to the participant (e.g., fingerprints, retinal scans). A record of the measured biological parameters may also be archived on the storage media as discussed herein.

The interactive presentation of an embodiment concludes either by way of the participant successfully demonstrating sufficient comprehension of the information provided or insufficient comprehension after repeated testing/retesting cycles. Upon conclusion of the participant's interaction with the interactive presentation system, both participant's interaction with the interactive presentation system and the visual record are archived on a storage medium, at block 22. In a preferred embodiment of the present invention, a record of the applicant's interaction with the interactive presentation system (e.g., the information provided, test questions provided and applicant's responses thereto) and the visual or audiovisual record of the participant are archived on the storage medium and correlated. The correlation of an embodiment provides that, upon retrieval and observation, at block 26, an observer is able to observe the information provided, test question provided and/or participant's response to the test question while simultaneously observing the visual record of participant's interaction with the presentation.

Figure 4:
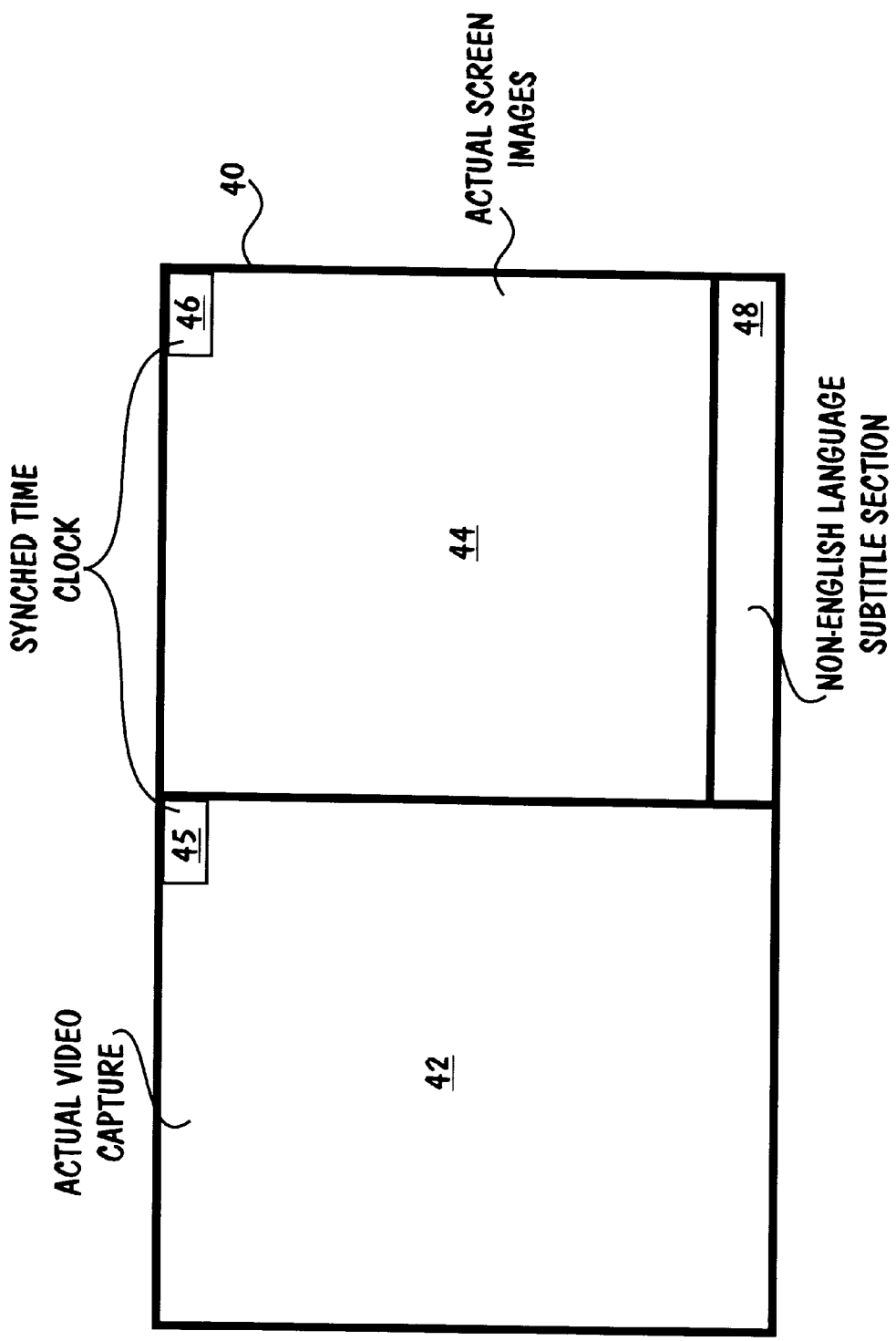
FIG. 4 is a diagram of a split-screen display device of an embodiment.

A number of display formats may be used for the replay including horizontal split-screen, vertical split-screen, and picture-in-picture. FIG. 4 is a diagram of a split-screen display format 40 of an embodiment. Such a screen 40 is split into two or more segments 42 and 44 preferably in such a way as to simultaneously view a real time video of the participant on one segment of the screen 42 while viewing the information conveyed, questions provided and the participants answers thereto on the other segment of the screen 44. A superimposed date-time clock 46 may be provided on either or both of the screen segments 42 and 44 to ensure the segments 42 and 44 are temporally simultaneous. Thus, one side of the output screen will display the images captured by the visual camera, in addition to the image of then recorded date-time clock. The other side of the output screen contains the entire interactive presentation as it occurred, including the participant's responses, and an image of the then recorded date-time clock.

Additional information including, but not limited to, text translation, the results of any system self tests, or subtitles may also be incorporated and displayed in one or more segments 48 of the display. Also, such simultaneous observation is not limited to the visual record of the participant and the participant's interaction with the interactive presentation. The simultaneous presentation of the interactive session may include display of the measurable outputs of all of the participant's interactions with the various components of the present invention during the learning session including, but not limited to, the participant's biological markers, written signatures, electronic signatures, and personal data (e.g., name, address).

The storage medium of an embodiment may include any durable, non-erasable, tamper-resistant/tamper proof storage media capable of recording the correlated record described herein. Suitable storage media include WORM (Write Once/Read Many) optical disk storage medium, CD-Rom disks, digital video disks, other laser video capture media, and tape back-up media including Zipp disks, Jazz disks, and Syquest, but are not so limited. Read/write compact or optical disc storage media are used because of the large amount of information that can be stored on a single disk and because of the durability of such disks. In an embodiment, each participant's correlated record may be stored on a unique disk, or, in the alternative, more than one participant's record may be stored on a single disk provided sufficient steps are taken to protect the participant's confidentiality.

Upon completion of a learning or education session, the participant is prompted to provide his or her signature, at block 28. The signature is archived on the storage media. While the participant's signature may be included on paper or other media and digitized for inclusion on the storage media, an embodiment provides the signature via an electronic means, such as a light pen or pressure pad. Where the participant's interaction with the interactive presentation system indicates the participant gained a desired or required level of comprehension of the information presented, their signature may be taken as another indicia of their understanding of the information and their willingness to assume such risks as disclosed by the presentation. Where the participant's interaction with the interactive presentation system indicates the participant did not gain a desired/required level of comprehension of the presented information, their signature may be taken as evidence that the participant engaged in the learning session.

When uncontrovertible proof is required or desired that participant did engage in the learning session, the participant may be requested or required to provide a uniquely personal marker in lieu of or in addition to the above described signature. The personal marker is recorded and archived, at block 22. Such uniquely personal markers include, but are not limited to, biological markers. The biological markers include fingerprints, toe/foot prints, corneal scans, and retinal scans, but are not so limited.

Where the archived record of one or more participants is maintained on storage media that is comprised of a number of discrete units (e.g., optical or compact disks), it is preferable to label such units for ease of filing and retrieval. The labels should be compatible with the selected storage media so as not to interfere with the retrieval of the information on the storage media. Further, the labels are durable and permanently affixed or otherwise associated with the storage media. For example, when the storage media is comprised of optical or compact disks, the label may take the form of a handwritten, typed, or computer-generated gummed label affixed to the optical or compact disk or to a storage case for such a disk.

The labeling should include sufficient identifying material for filing and retrieval of a particular unit. While the label could include information about the participant (i.e. name, address) in text or written form, an embodiment provides a labeling system which protects the confidentiality of the participant's record. For example, where the label includes information, such as the name and address of the participant in visually observable texture or written form, individuals involved in the filing and retrieval of the storage media would be able to read the label and associate an individual participant with their record. In order to prevent this and to protect the confidentiality of the participant, the identifying material on the label may be of at least one type selected from a group comprising alpha, numeric, and alpha-numeric information which identifies the individual participant and provides the desired information on the label in such a way as not to be readable or comprehendible by individuals observing the label. With such a system, the participant is then only identified by comparing the identifying material on the unit with a table or other data collating system which correlates the identifying material with an individual participant, and access to such a table may be restricted to protect the participant's confidentiality.

In an alternative embodiment of the present invention, the units of the storage media may be provided with barcoded identification tags, at block 32. Barcoded identification tags protect the participant's confidentiality while providing compatibility with many automated storage and retrieval devices which automatically store and retrieve by reading barcoded information. Furthermore, any confidential record management system, apparatus, or processes may be used that provides secure, confidential management of the participant's record.

A permanent archiving apparatus is provided herein at the same physical location or site as the information conveying device and visual and interactive presentation recording devices. For purposes of the discussion herein, unless otherwise clear from the context, the information conveying device, visual recording, and interactive recording devices are hereinafter collectively referred to as the "information conveying/recording operation".

The archiving of electronic records is memory intensive, particularly where such information includes digitized video information. In an embodiment, system efficiency is improved by providing a central location for receiving digitized records and downloading the records to the selected storage media of the central location. This results in the use of fewer archiving devices where the information is provided to participants at different sites, such as for example, in the various departments of a hospital or at different hospitals within a given hospital system. Furthermore, the central records location provides for improved data security because personnel involved in archiving the data are substantially removed from the participant ensuring an additional layer of confidentiality for the participant.

However, where the information conveying/recording operation and the archiving operation are conducted at different sites, the transmission of the record of the learning session from one site to the other raises certain concerns. Among those concerns is that the transmitted data must be transmitted rapidly, inexpensively, free of errors, and with sufficient security. In addition, some temporary archiving should be provided at the site of the information conveying/recording operation until confirmation is received of the receipt and error-free archiving of the record at the site of the permanent archiving operation. An embodiment provides electronic downloading of session records to the site of the permanent archiving operation, or the record repository. The electronic downloading may occur via the Internet, a dedicated local area network, leased private or semi-private data transmission lines, and combinations thereof, using encryption or other secure means, but is not so limited. The record repository of an embodiment uses security procedures to safeguard and limit access to the records stored therein.

Figure 2:
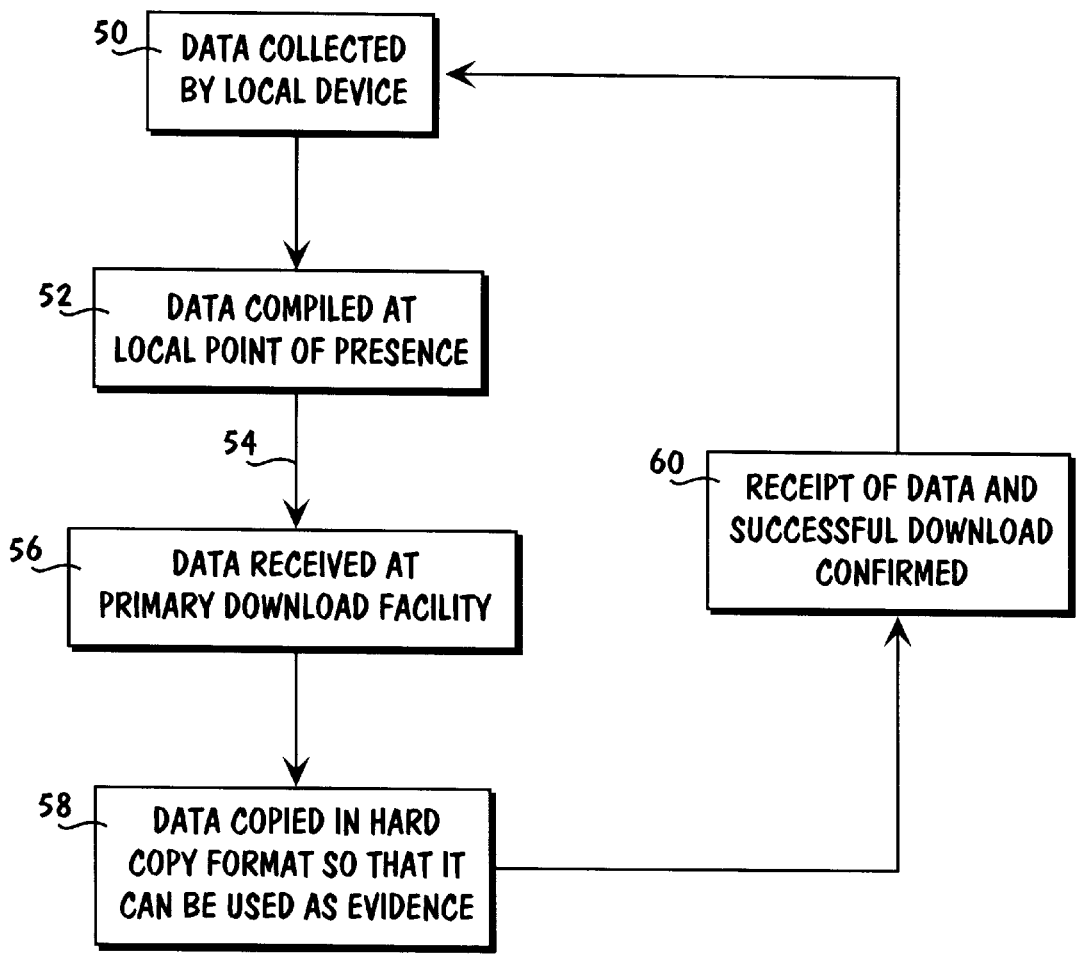
FIG. 2 is a flow diagram of a method of relaying collected data to a remote storage facility in an embodiment.

FIG. 2 is a flow diagram of a method of relaying collected data to a remote storage facility in an embodiment. Session data is collected by the information conveying/recording device, at block 50. The session data may be compiled at the same site, at block 52. The data is encrypted and conveyed electronically 54 to a second site, a record repository, as described herein. The encrypted data is received at the record repository, at block 56, whereupon it is archived on the storage media, at block 58. In an alternate embodiment, the data is at least temporarily archived at the first site until receipt and confirmation of a successful downloading at the record repository is transmitted to the first site, at block 60. Upon receipt of the confirmation, the temporarily archived data at the first site may be optionally erased or otherwise destroyed. In the alternative, the data may be permanently archived at both the first and second sites to provide a redundant system. However, where confidentiality of the record is a concern, steps similar to those outlined above with regard to protecting the participant's confidentiality should be maintained at both the first and second sites.

Figure 3:
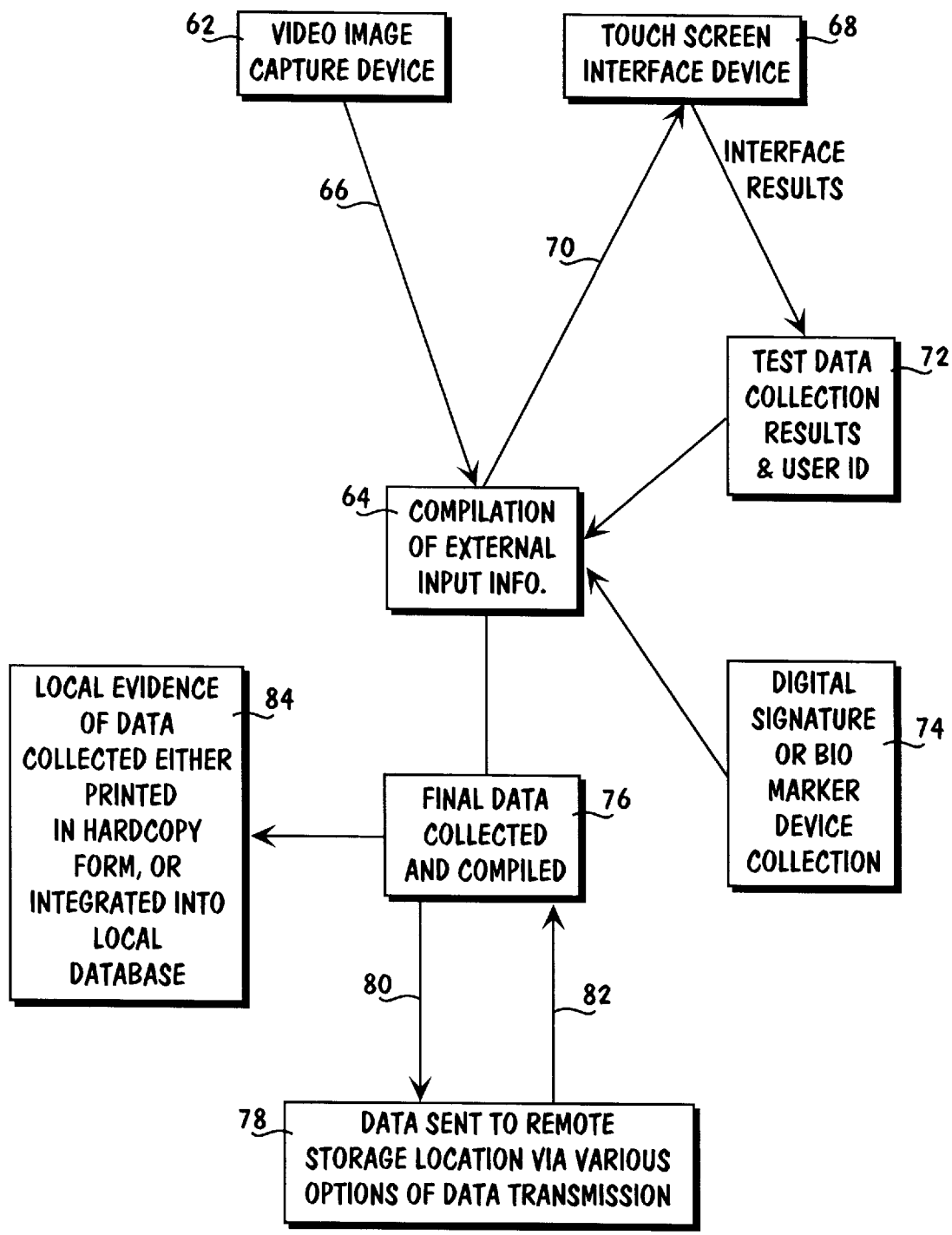
FIG. 3 is a schematic of an apparatus for obtaining informed consent in an embodiment.

FIG. 3 is a schematic of an apparatus for obtaining informed consent in an embodiment. A visual image capture device (e.g., a digital video camera) 62 is coupled to an information conveying/recording device 64 (e.g., a computer) in such a manner as to enable the visual image capture device to download 66 a visual record to the information conveying/recording device 64. The information conveying/recording device 64 provides selected information 70 to an output device 68 (e.g., an audio/visual monitor). Such information may be in a narrative form or in the form of an interactive presentation as described herein. Where the information is in the form of an interactive presentation, the output device 68 is fitted with an input mechanism to receive input from a participant as appropriate during the interactive presentation. An example of a suitable input device is the touch screen described herein. The information conveying/recording device 64 provides, in the interactive presentation form, testing inquiries that require a response by a participant, but is not so limited. The test data may then be returned to the information conveying/recording device 64 directly or conveyed to a data collection device 72 (e.g., a computer or other high speed access digital media storage device) which in turn relays the test data to the information conveying/recording device 64. The information conveying/recording device 64 of an embodiment is provided with a real-time clock and a day/date indicator which records the date and time of the recording of both the visual record and the participant's interaction with the interactive presentation system for subsequent display as described herein.

In an alternate embodiment, the information conveying/recording device 64 may be in communication with a marker device 74 (e.g., a digital signature device or biological marker device) to input such authenticating information from the marker device 74 into the information conveying/recording device 64. The recorded visual information and test data may be compiled in a correlated fashion using an onsite archiving device 76. The archiving device 76 may provide temporary or permanent archiving. In an embodiment, the correlated record is sent to the record repository 78 at a second site via the data transmission devices described herein, which in turn provides confirmation of an error-free receipt 82 back to the archiving device 76.

In another embodiment, a device 84 for evidencing collection of the visual and interactive presentation data at the first site may be in communication with the archiving device 76 to provide confirmation of the record collection at the first site. Such evidence may be in the form of a printed hardcopy notice or by updating a database associated with the device 84. An encryption device (not shown) may be used that is a separate unit of the system or that is incorporated into one of the system devices, for example the archiving device 76 or the information conveying/recording device 64.

Figure 5:
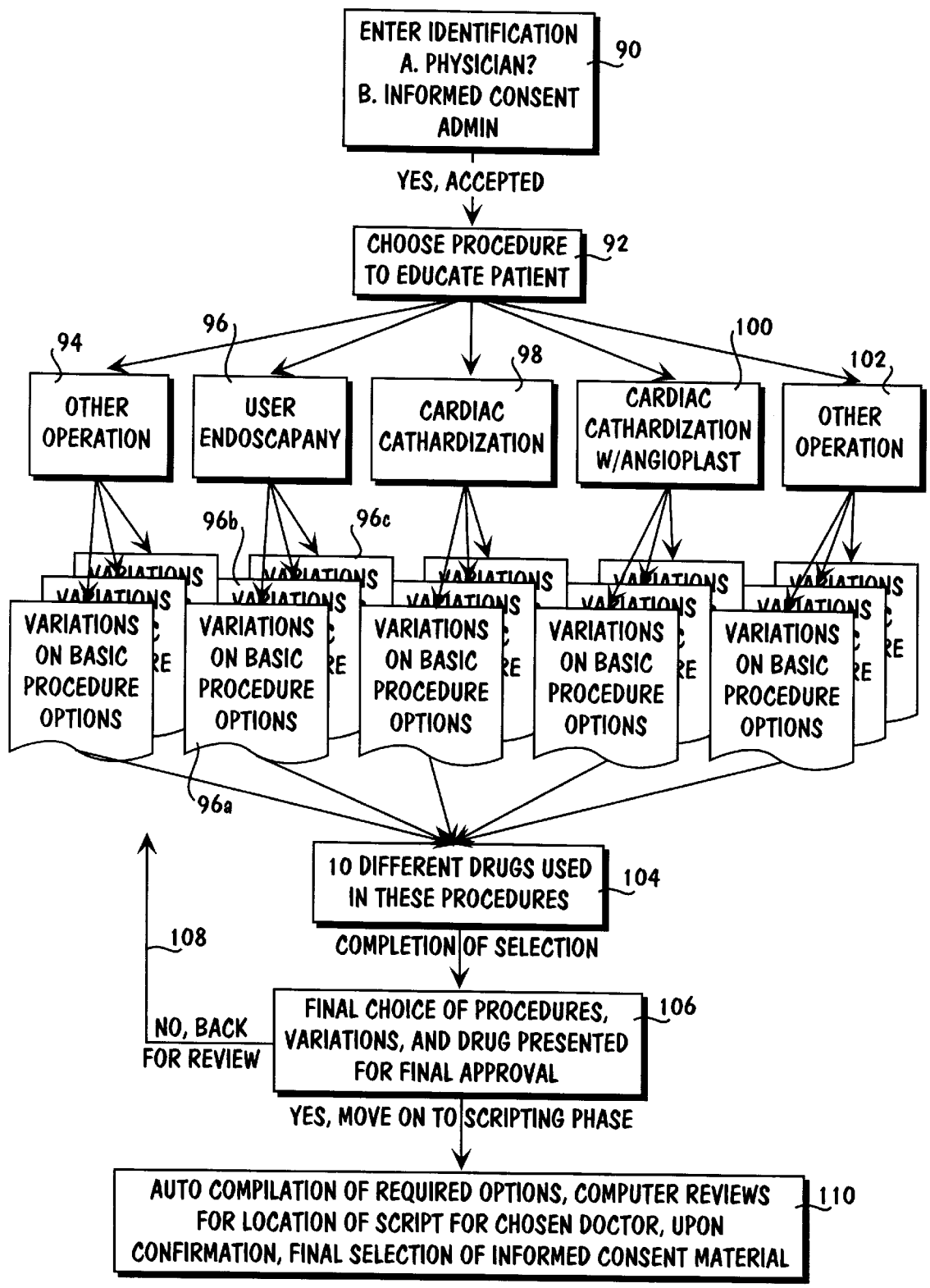
FIG. 5 is a flow diagram of the provision of medical information and the receipt of an authenticated informed consent in an embodiment.
Figure 6:
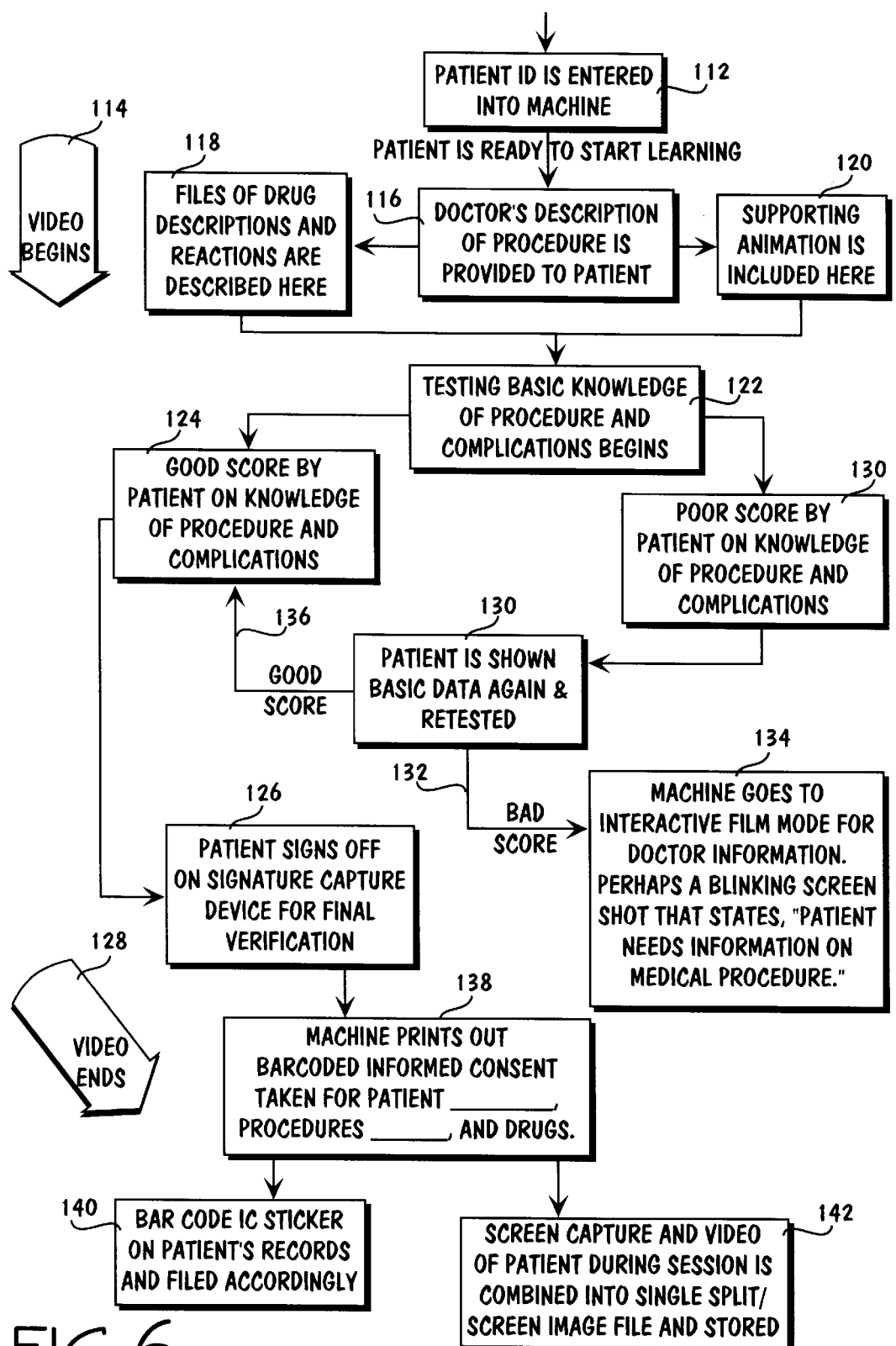
FIG. 6 is a continuation of a flow diagram of the provision of medical information and the receipt of an authenticated informed consent in an embodiment.

FIGS. 5 and 6 are flow diagrams of the provision of medical information and the receipt of an authenticated informed consent in an embodiment. The provision of medical information and the receipt of an authenticated informed consent of an embodiment generally comprises the steps of: (1) energizing an interactive presentation; (2) entering administrative information into the interactive presentation permitting the physician to interface with the system; (3) re-entering administrative information if required; (4) choosing a desired subject matter for presentation; (5) explaining collateral subject matter related to the subject matter selected; (6) presenting a final overview of the desired subject and any collateral subject matter for acceptance by the physician; (7) entering a scripting phase to collate the information selected by the physical for presentation to the patient as an interactive presentation; (8) compiling any required options into the presentation; (9) completing the scripting phase; (10) entering a patient's identification data into the interactive presentation; (11) positioning a patient before the interactive presentation to prepare the patient to interact with the interactive presentation; (12) conveying the scripted information to the patient, preferably from a video and data recording means while simultaneously visually or otherwise recording the patient and recording the information presented during the interactive presentation and recording the patients inputted responses to questions regarding the information presented as described below; (13) providing a means for the patient to input data in the form of answers to questions regarding the information presented to test the patient's comprehension of the information presented; (14) prompting the participant to answer a series of preformatted questions; (15) repeating portions of the interactive presentation with the same information, new information or combinations thereof if the patient's number of correct answers is below a predetermined threshold; (16) terminating the interactive presentation if the patient continues to perform below the predetermined threshold or if the patient's number of correct answers is above a predetermined threshold; (17) prompting the patient for an electronic signature; (18) stopping the data and video recording means; (19) printing identifying, preferably bar coded labels; (20) positioning a bar coded label on the participant's medical records; (21) making a consolidated, correlated, non-erasable, tamper-resistant record of the video, the interactive presentation transactions, and authenticating information; (22) optionally making a backup copy of the consolidated, correlated non-erasable, tamper-resistant record; (23) encrypting the non-erasable, tamper-resistant record; (24) downloading the consolidated non-erasable, tamper-resistant record; and, (25) positioning a bar coded label on the consolidated non-erasable, tamper-resistant record.

With reference to FIGS. 5 and 6, operation begins at block 90, at which either the physician or administrator in charge of the learning session enters identifying information in order to activate the system. In the following discussion the term physician will be used, but healthcare facility administrators or other individuals qualified and authorized to administer the system are included within that term. The input of identifying information by which authorized personnel access the system protects the integrity of the system by minimizing the chance of intentional or inadvertent corruption of patient information. If the identifying information for the physician is accepted, the physician is then prompted or permitted to select the information desired to be conveyed to the patient, at block 92. A few surgical procedures for which information is available in the system are illustrated at blocks 94, 96, 98, 100 and 102, but the embodiment is not so limited. Information regarding common variations on the basic surgical procedures may also be included in the system, at blocks 96a, 96b, and 96c. Information regarding the surgical procedures may have been previously inputted by a physician in the form of textual material, visual material or audiovisual material.

Alternatively, standardized information may be provided, in lieu of or in addition to information regarding the surgical procedures, to ensure that each patient receives the same information when standardization is desired or required. Where standardized information is selected, one important advantage of an embodiment is that the results of the testing of several patients' understanding of such information can be examined by the testing described herein in order to identify which standardized presentations are being readily understood by the majority of patients and, conversely, identifying those which are not. The information may be provided in narrative form or as an interactive presentation maintained on a device suitable for the storage and presentation of such information. Suitable devices include computers and computer databases, but are not so limited.

When the subject matter has been selected for the patient by the physician, additional information like information regarding the drugs, chemicals, or medicines to be used in the selected surgical procedure may also be provided as part of the interactive presentation, at block 104. A final overview of the procedure, any variations, and the drugs involved are presented for final inspection to the physician, at block 106. If the information in the final overview is not the proper information or is incomplete, the process can be returned 108 to the selection of subjects and the process repeated. If the final overview contains the correct information, the physician approves the selection and the appropriate information is prepared for presentation to the patient. More particularly, a scripting phase 110 is initiated, comprising an auto-compilation of the options specified above in terms of the information the physician has selected for presentation to the patient.

After the selected information is compiled by the information conveying device, or while the device is compiling the relevant information during the scripting operation, either the patient or the physician may enter information identifying the patient such as the patient's name, address, phone number, and social security number. Furthermore, the physician or patient may enter a patient identification number in addition to or in lieu of the identifying information for confidentiality purposes, at block 112. Optionally, the patient may be asked to confirm the accuracy of the personal information, whereupon an affirmative response may be utilized to activate other features of the invention including, but not limited to, the activation of a system self-diagnostic test of the critical system components. Other features, such as a tamper-indicating encryption stamp or other method to identify intentional or unintentional corruption of the data selected for presentation or the patient's responses thereto can also be added/activated. The patients' responses to the questions described herein may be recorded simultaneously with a visual record of the patient's interaction with the questions, in real time, along with a running date-time clock to authenticate the presentation to the patient and the patients' response thereto.

At this point, the patient is prepared for the presentation and the presentation is conveyed to the patient. Where the information being provided includes visual information, the visual information is provided 114. The interactive presentation includes the preselected subjects. An introduction by the physician overseeing or performing the procedure may be presented along with a description of the procedure, at block 116. Where drugs are to be administered, drug descriptions and associated information may be provided, at block 118. Similarly, supporting audio, graphics, animation or the like may be provided, at block 120.

In an embodiment, the participant may be presented with questions on the presented material by the interactive presentation, at block 122. The questions may be presented before, during, or after the interactive presentation, or any combination thereof. Questions presented before the presentation are presented to asses the patients preliminary level of understanding. The participant's answers are scored by the system and, if the patient's score indicates a desired or required level of comprehension of the material presented, at block 124, the patient is directed at the end of such presentation to provide his or her signature. The signature of an embodiment is captured electronically by way of a digital signature device 126, and the presentation of information ends 128. However, if the patient's test score is not satisfactory, at block 130, either repeated or new information regarding the relevant subject matter is provided and the patient is retested, at block 132.

The questions are used during the presentation in order to identify with particularity where the patient is having trouble comprehending the information and to confirm those areas where comprehension is satisfactory. This, in turn, permits presentation of additional reinforcing information of a very focused nature directed to the patient's specific areas of unsatisfactory comprehension, at block 132. If the participant's retest score is again unsatisfactory after a pre-programmed number of re-education attempts, the interactive presentation session is terminated. At this point, a medical professional is consulted, and individual counseling may be provided to the patient while the visual or audio/visual recording continues, at block 134. The patient may be returned to the interactive system if warranted in the opinion of the physician, or such individual counseling may take the place of any further patient interaction with the interactive presentation. In the alternative, with a satisfactory retesting score the patient is prompted to provide their signature, at block 124, indicating understanding of and consent to the procedure.

The interactive presentation ends after the participant signs their name. In an embodiment, the session data including the interactive presentation provided to the patient and the visual record of the patient's interaction with that interactive presentation is archived. The recorded and archived session data is correlated, and may include a real-time clock and day/date indicia to ensure synchronized playback. The storage media on which the record is archived may be provided with identifying information in the form of a barcode tag affixed to the storage media, at block 138. The identifying material may include information summarizing the patient's identifying information or number, the surgical procedure presented, and/or the drugs described. Other pertinent information may be included as well including the date and time the information was presented and the attending physician, but is not so limited.

In an embodiment, two identical barcode tags may be provided, at block 140. The first barcode tag is attached to the storage media (e.g., a non-erasable video or digital record of the learning session). The second barcode tag is affixed in the patient's written and/or electronic medical records to provide confirmation in the patient's record that the patient was provided with the information for which the physician sought the patient's informed consent.

The record of the session may be archived at the site of information conveyance or may be transmitted to an off-site record repository as described herein. Where the session record is transmitted off-site, the barcode tag or other labeling means may include information confirming that the patient's session was encrypted before transmission. In another embodiment where the record is not transmitted, but is permanently archived at the site of information conveyance, the record may be encrypted to increase patient confidentiality. Further, where the off-site record repository is designed to provide confirmation of successful receipt and downloading back to the original site of information conveyance, such confirmation may be provided in several forms, including a written form, which is also placed in the patient's written medical file. When later observation of the patient session record is required or desired, the session information may be retrieved and displayed using a format described herein, at block 142.

While the embodiments described herein are directed to medical applications for purposes of illustration, the invention is by no means limited to medical applications. The method and apparatus of the present invention can also be used in conjunction with many other activities whenever authentication of the conveyance and understanding of information is required or desired. Non-limiting examples include requiring informed or knowing consent or waiver of the assumption of risks associated with activities such as renting jet skis or other watercraft, driving or renting sports cars, renting equipment and vehicles, skydiving, horseback riding, receiving Miranda warnings, and submitting to breathalyzer examinations. Therefore, the particular embodiment of the invention described above should not be considered as limiting to the scope of the invention.

It can therefore be seen that the embodiments described herein provide an apparatus and a method of employing the apparatus to educate, confirm exposure to and comprehension of the educational material, to provide a permanent record of the same including the ability to authenticate the integrity of the record, add credibility to the process used to create and provide the record, and help ensure individual privacy rights. The apparatus uses an interactive presentation to facilitate a participant's comprehension while simultaneously creating a non-erasable, tamper-resistant record which can be stored separately or encrypted and sent to a remote location. The invention provides a process applicable to a broad range of activities and provides evidence and proof of understanding of the risks involved with such activities and a fully-documented, informed consent process which is customizable and individual in focus.

In furtherance of the medical applications, a Virtual Interactive Teaching And Learning (VITAL) Center is provided herein that offers a solution to the medical malpractice dilemma by using computer and video technology to improve patient education and the informed consent process. The VITAL Center offers patients a comprehensive, interactive presentation about their procedure prior to discussing concerns with their physician. As such, the VITAL Center of an embodiment will educate patients by providing substantive, comprehensive, uniform, and up-to-date information about both their condition and the proposed treatment plan. This knowledge will foster the patient-physician relationship. Furthermore, the VITAL Center will provide the healthcare provider and risk manager with a visual, written and oral record of the patient's interactive participation in the educational process. Consequently, the VITAL Center of an embodiment provides the following advantages over the typical informed consent process: provides a foundation of knowledge for more meaningful communication between patients and physicians; allows for more personal physician interaction with patients; helps establish a physician-patient relationship that is built on understanding and trust; offers accurate and up-to-date medical information in a multitude of languages; ensures comprehension by the patient before informed consent is granted; thoroughly documents the education and informed consent process; and, enhances organizational efficiency.

The VITAL Center of an embodiment provides patients with standardized information in a multimedia format about each of a number of medical and surgical procedures. The VITAL Center provides information and answers questions for each procedure according to the "Guidelines on Questions Patients Should Ask Prior to Elective Surgery", as set out by the American College of Surgeons. In order for patients to understand the nature of the procedure to be performed and give their permission for the procedure, the VITAL Center formats each presentation to answer the ten questions put forth by the American College of Surgeons.

The VITAL Center uses a multimedia interactive educational process to present information to the patient and the patient's family or legal guardian via a video presentation. The VITAL Center provides the patient with the most current information regarding the proposed procedure, including risks and benefits, alternative treatments, a review of the procedure, guidelines for pre- and post-procedure care and the medications that may be used during the procedure. The power of the VITAL Center lies in its animations and illustrations of the procedure, which surpass mere verbal explanations. This process enables patients to gather their thoughts, formulate questions and feel better prepared for the conversation with their physician. The patient can review the information at their own pace until it is sufficiently understood and they can demonstrate a measurable level of acceptable understanding of the proposed treatment.

The VITAL Center is not designed to replace the pre-procedure consultation with the attending physician, but to precede and enhance the consultation. A VITAL Center presentation provides the patient with the most current information regarding a procedure. By having basic information prior to the visit with the doctor, a patient will be able to discuss with the doctor the issues that are important to the patient, making the time spent with the doctor more informative and productive.

By providing this baseline education to patients and their families, physicians can focus more on reducing patient anxiety and addressing each patient's specific concerns. This quality time helps establish patient-physician relationships that are based on mutual understanding and trust. The patient's comprehension of and consent to the procedure is electronically analyzed and recorded. The healthcare provider can be confident that the patient has been provided with an appropriate, standardized, sound medical/legal description of the proposed procedure. Thus, the VITAL Center improves patient education, enhances patient-physician interaction, and standardizes the education and informed consent process, thereby reducing costs industry-wide.

Figure 7:
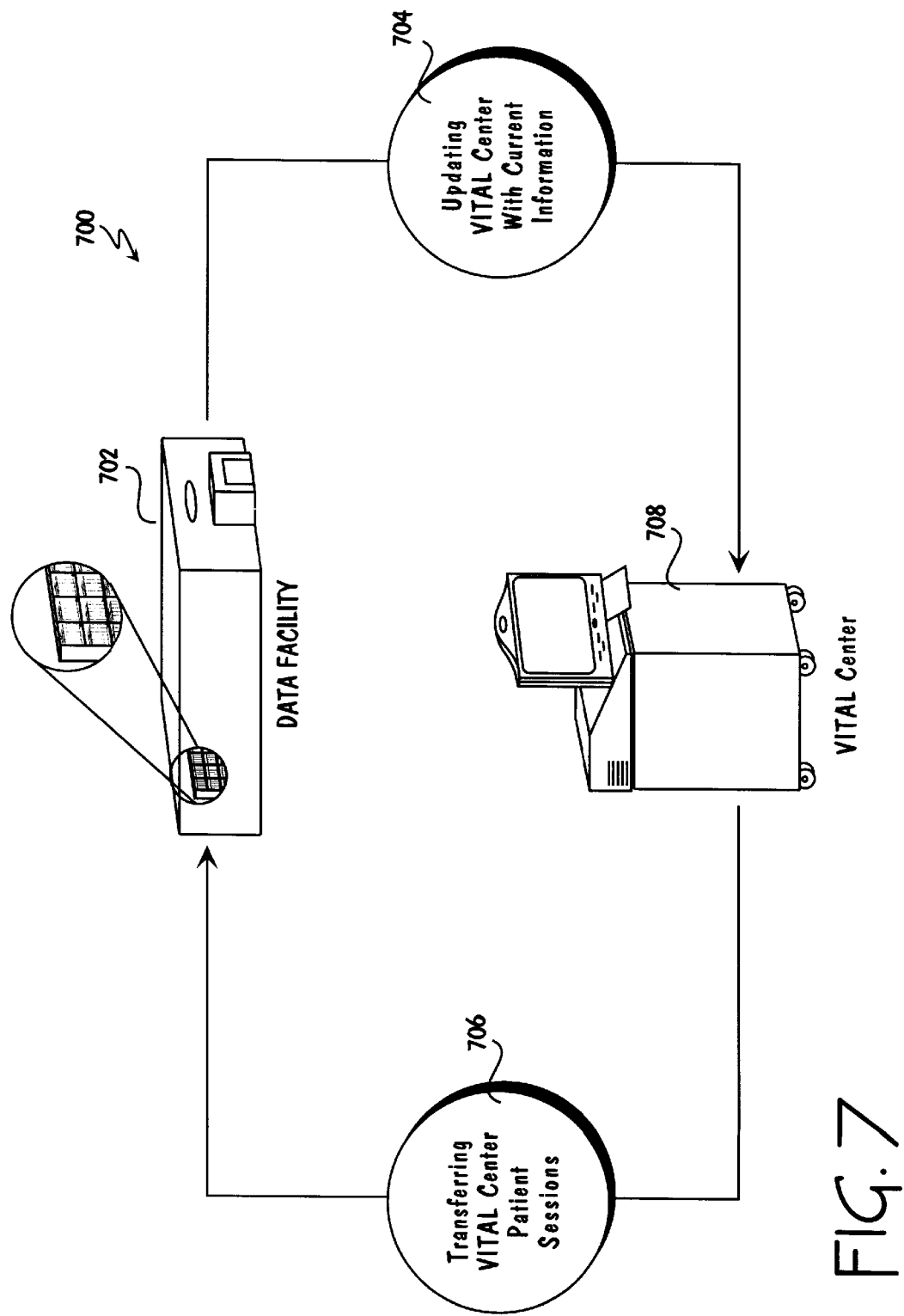
FIG. 7 is a system for obtaining informed patient consent of an embodiment.

FIG. 7 is a system 700 for obtaining informed patient consent of an embodiment. The system 700 comprises a data facility 702 coupled to transmit information to 704 and receive information from 706 at least one VITAL Center 708. The transfer of information among the data facility and the VITAL Centers may be performed using a dedicated network, an Internet connection, or a wireless network, but is not so limited. In operation, on a daily or other periodic basis, each VITAL Center 708 is coupled to the network for a two-way transfer of data 704–706. The transfer of data includes the transmission of patient education sessions 706 from the VITAL Center 708 to the data facility 702. The transfer of data also includes transfers in which the data facility 702 automatically transmits 704 presentation updates to the VITAL Center 708. The network can exist independently of, or be integrated into an existing healthcare facility information systems network. In an embodiment, the network is a proprietary virtual private network, but is not so limited.

During the transmission 706 of recorded patient sessions, all recorded and stored patient sessions are securely transmitted to the data facility 702 using encryption technology. This encryption ensures maximum protection of patient privacy and the security of the network. Encryption of an embodiment uses a standard private/public key system, wherein a decryption key is provided to the patient and healthcare provider. Once received at the data facility 702, the encrypted data is archived onto optical disk storage media. Magneto-optical disks of a write once/read many type may be used for permanent storage, but are not so limited. Through a barcoding system, each videotaped patient session can be easily filed and retrieved if necessary. An acknowledgment of obtainment of the informed consent is also provided to the healthcare provider for inclusion in the patient file.

The transfer 704 of updated information includes transferring updates to each VITAL Center 708 from the data facility 702, ensuring that the information contained in the VITAL Center 708 is up-to-date and accurate. Updates may include new procedures, pharmaceuticals, and statistics, or simply modifications to the existing information. Utilizing this network strategy, each VITAL Center 708 is able to maintain current and consistent information automatically, regardless of its location. This updating process is designed to facilitate efficient maintenance of the VITAL Center 708 with a minimum disruption to the healthcare staff and medical facility.

Figure 8:
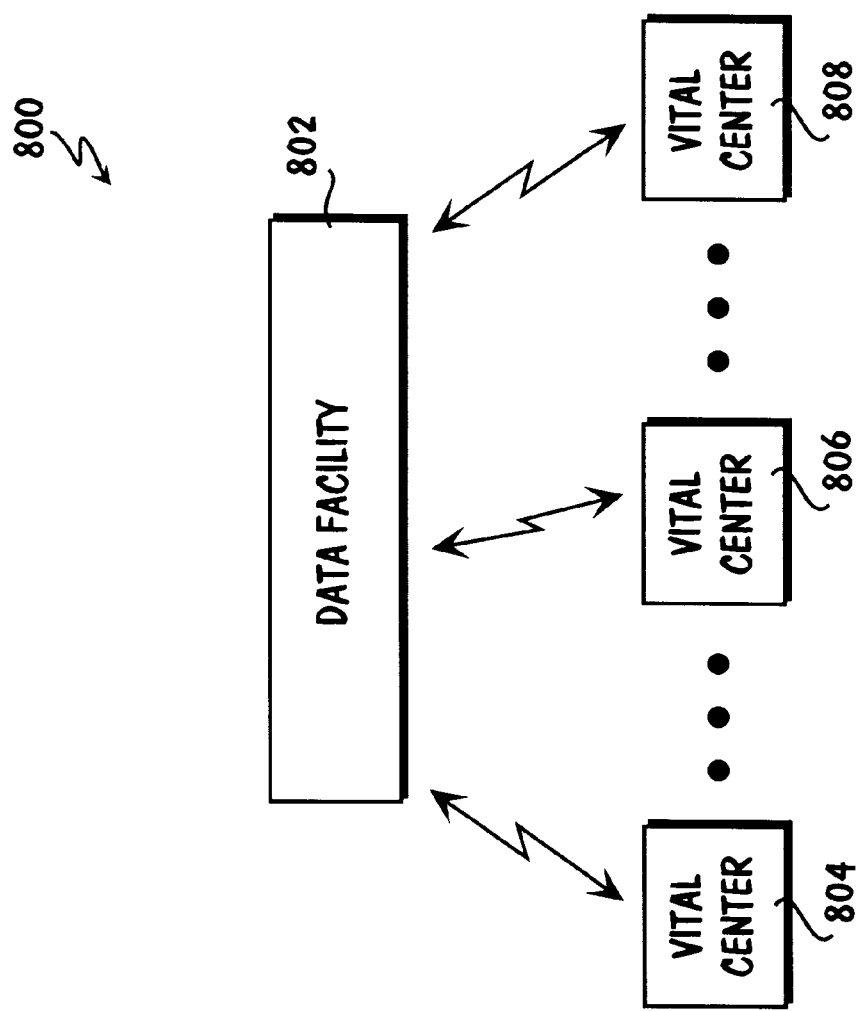
FIG. 8 is an alternate embodiment of a system comprising a number of VITAL Centers and a data facility.

FIG. 8 is an alternate embodiment of a system 800 comprising a number of VITAL Centers 804–808 and a data facility 802. The system 800 includes a number of VITAL Centers 804–808 at a number of locations coupled to a central data facility 802 using networks as described herein. The VITAL Centers 804–808 may be co-located at the same facility or campus. Furthermore, the VITAL Centers may be located within different departments of a healthcare provider, where the different departments are located at the same facility, different facilities at the same geographical location, or different facilities in different geographical regions.

Figure 9:
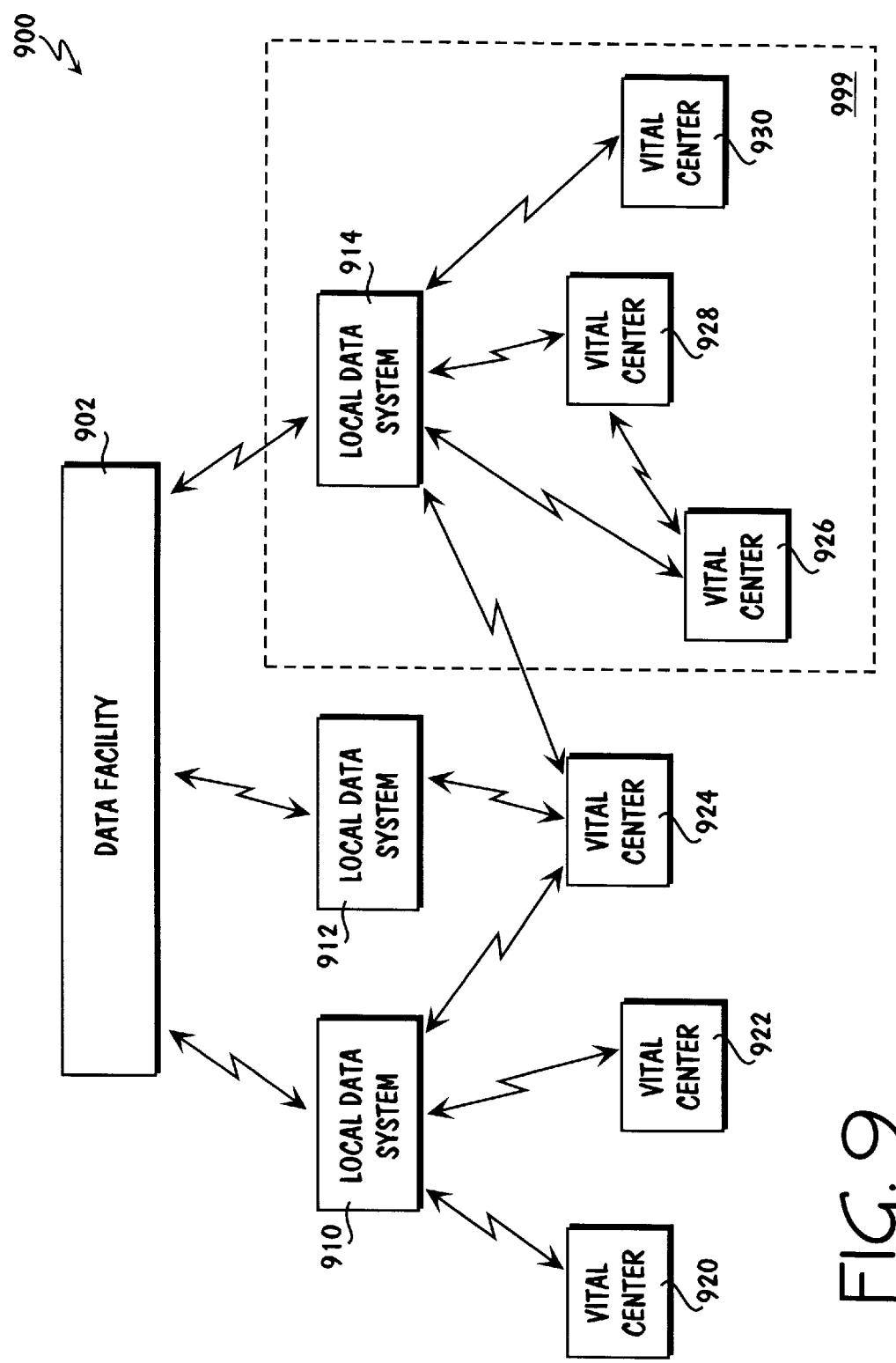
FIG. 9 is another alternate embodiment of a system comprising a number of VITAL Centers, local data systems, and a data facility.

FIG. 9 is another alternate embodiment of a system 900 comprising a number of VITAL Centers 920–930, local data systems 910–914, and a data facility 902. The system 900 comprises a number of VITAL Centers 920–930 at a number of locations coupled to a number of local data systems 910–914. For example, a local data system 910 may support a number of VITAL Centers 920–922 within a specific facility or geographical region. In another example, a local data system 914 may be located at a healthcare facility 999 to support a number of VITAL Centers 926–930 operated by that healthcare provider in one or a number of their facilities. In still another example, a mobile or roaming VITAL Center 924 may be supported by any local data system 910–914 that can be accessed. The local data systems 910–914 are coupled to a central data facility 902 using networks as described herein. Alternately, any VITAL Center 920–930 may be coupled directly to the central data facility 902 without going through a local data system 910–914. The local data systems 910–914 may archive and store information transferred from the VITAL Centers 920–930, but are not so limited. Furthermore, a VITAL Center 926 operating within a healthcare facility 999 may access the on-site local data system 914 or the central data facility 902 using another on-site VITAL Center 928.

It is noted that the VITAL Center of an embodiment may be integrated with other equipment of a healthcare facility. For example, the VITAL Center could be integrated with or coupled to information systems of the facility. The VITAL Center could also be integrated with or coupled to patient diagnostic equipment. Furthermore, the VITAL Center could be integrated with a patient record system comprising wireless portable data devices that support the provision of patient record information to healthcare professionals as well as the intake of patient vital statistics, symptoms, and conditions by healthcare professionals.

Figure 10:
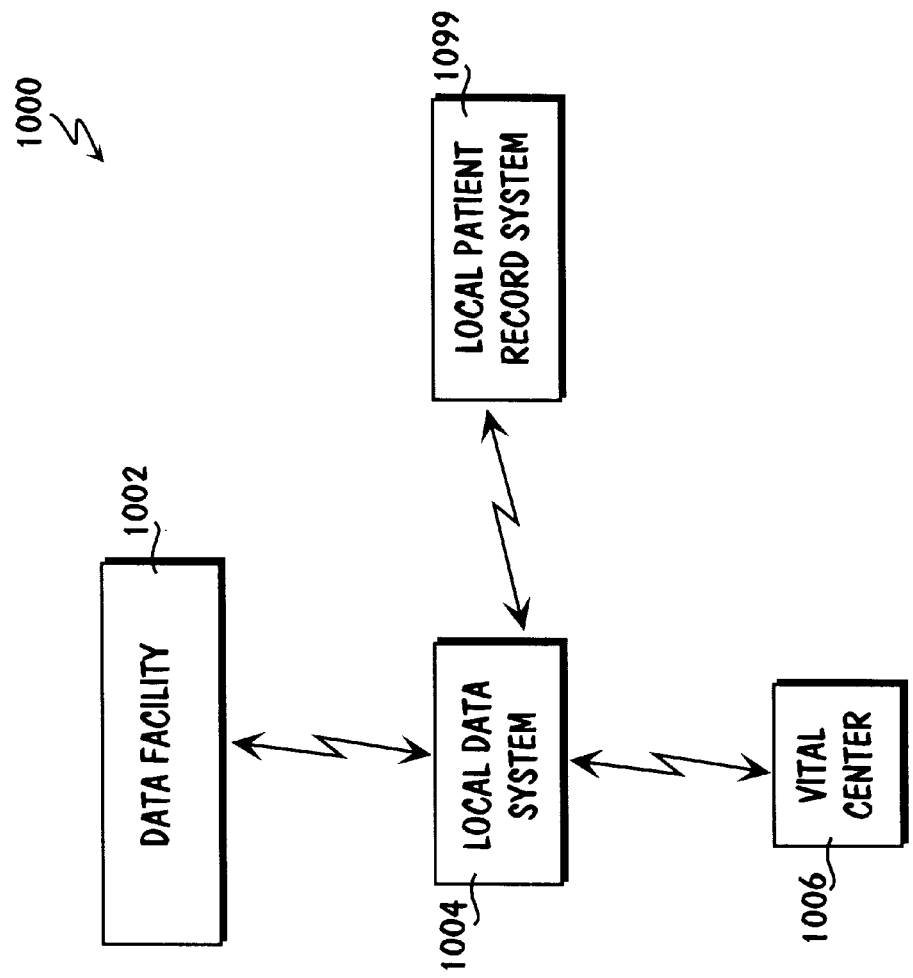
FIG. 10 is still another alternate embodiment of a system comprising a VITAL Center, a local data system, a local patient record system, and a data facility.

FIG. 10 is still another alternate embodiment of a system 1000 comprising a VITAL Center 1006, a local data system 1004, a local patient record system 1099, and a data facility 1002. In this system, the patient record system 1099 of a healthcare facility is coupled to a local data system 1004 or, alternately, to a VITAL Center 1006. The patient record system 1099 may be used to provide patient information and records to the VITAL Center 1006 for use in automatically filling out the patient records of the VITAL Center 1006. Furthermore, the VITAL Center 1006 may provide electronic patient information directly to the patient record system 1099 as well as to the data facility 1002. The VITAL Center 1006 is coupled to the local data system 1004, and the local data system 1004 is coupled to the data facility 1002 using networks as described herein. Alternately, the VITAL Center 1006 may be coupled directly to the data facility 1002 or the patient record system 1099.

Figure 11:
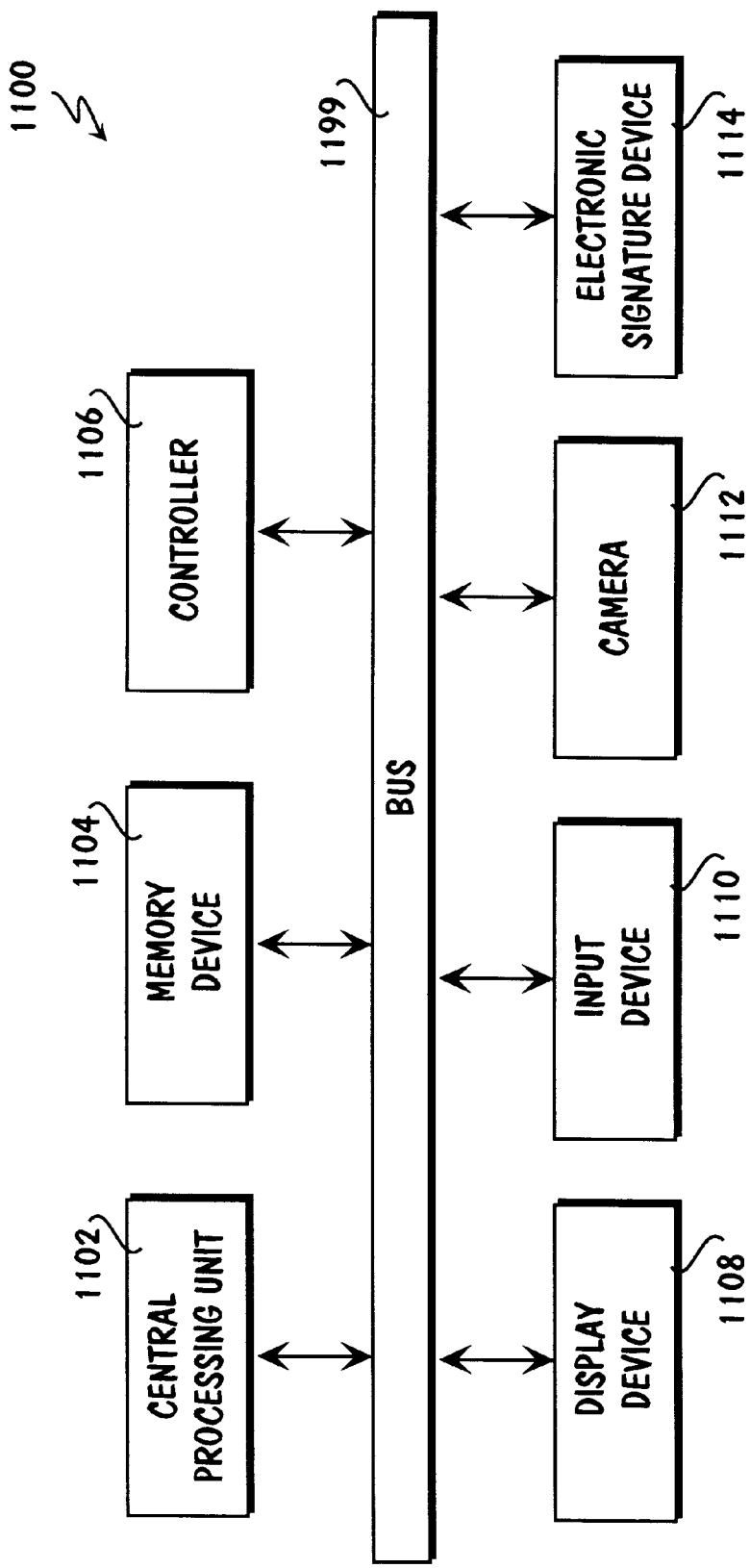
FIG. 11 is a block diagram of a VITAL Center of an embodiment.

FIG. 11 is a block diagram of a VITAL Center 1100 of an embodiment. The VITAL Center 1100 comprises at least one central processing unit (CPU) 1102, at least one memory device 1104, at least one controller 1106, at least one display device 1108, at least one input device 1110, at least one camera 1112, and at least one electronic signature device 1114. The components 1102–1114 of the VITAL Center 1100 may be coupled using a bus 1199, but are not so limited. Furthermore, the components 1102–1114 may each be coupled to the CPU 1102. The display device 1108 of an embodiment comprises a touch-sensitive screen for use as an input device, but is not so limited. The touch-sensitive screen of the processor-based system enables the system user to view the interactive information provided and touch the screen to provide the requested input. The input device 1110 comprises a device selected from a group including a mouse, a joystick, a keyboard, and a microphone. The microphone may be used in an embodiment in combination with a speech or voice recognition system, thereby providing for system control and information entry using voice commands. The camera 1112 comprises a device selected from a group comprising still cameras, digital cameras, video cameras, and digital video cameras. Furthermore, the camera function may be electronically integrated with the pixel electronics of the display screen.

Figure 12:
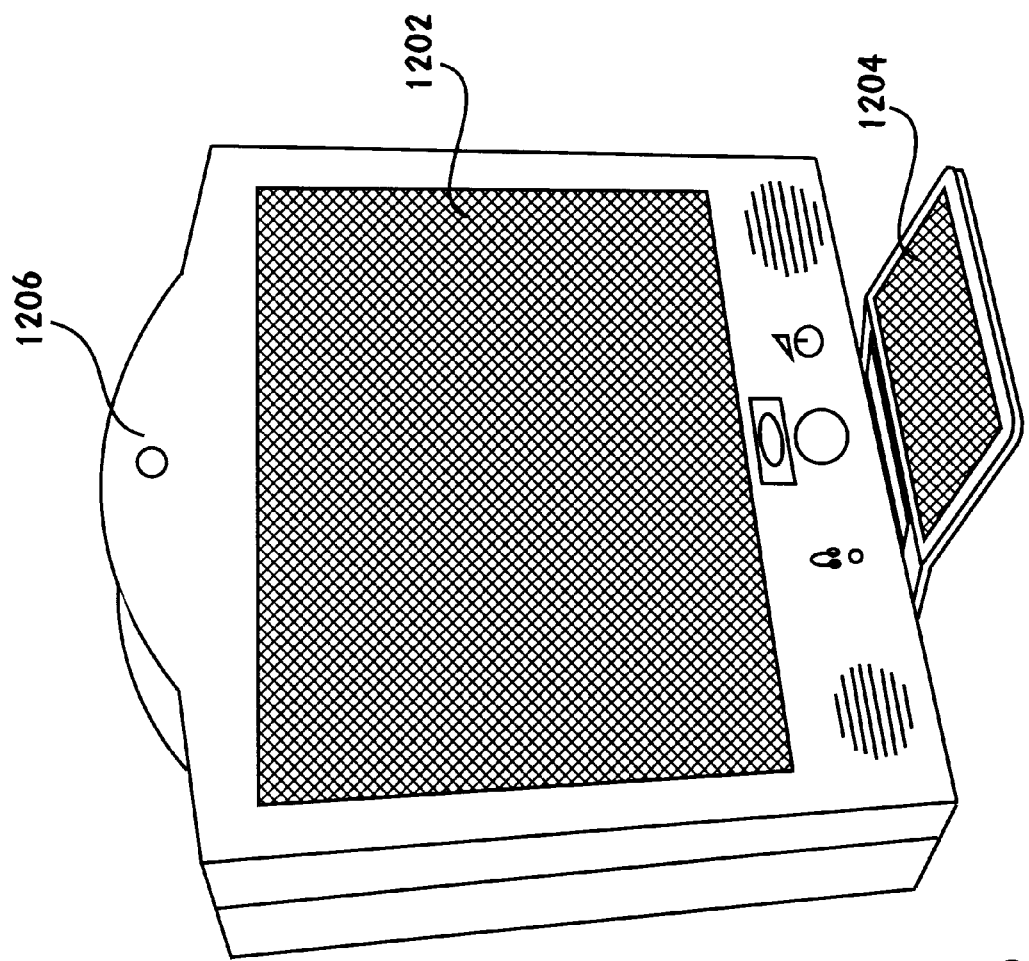
FIG. 12 is a VITAL Center touchscreen of an embodiment.

FIG. 12 is a VITAL Center touchscreen 1200 of an embodiment. The touchscreen 1200 comprises a flatscreen display 1202 with a touch-sensitive screen interface. The electronic signature capture device 1204 is coupled to the touchscreen 1200. In an embodiment, a camera 1206 is provided in the touchscreen 1200.

Figure 13:
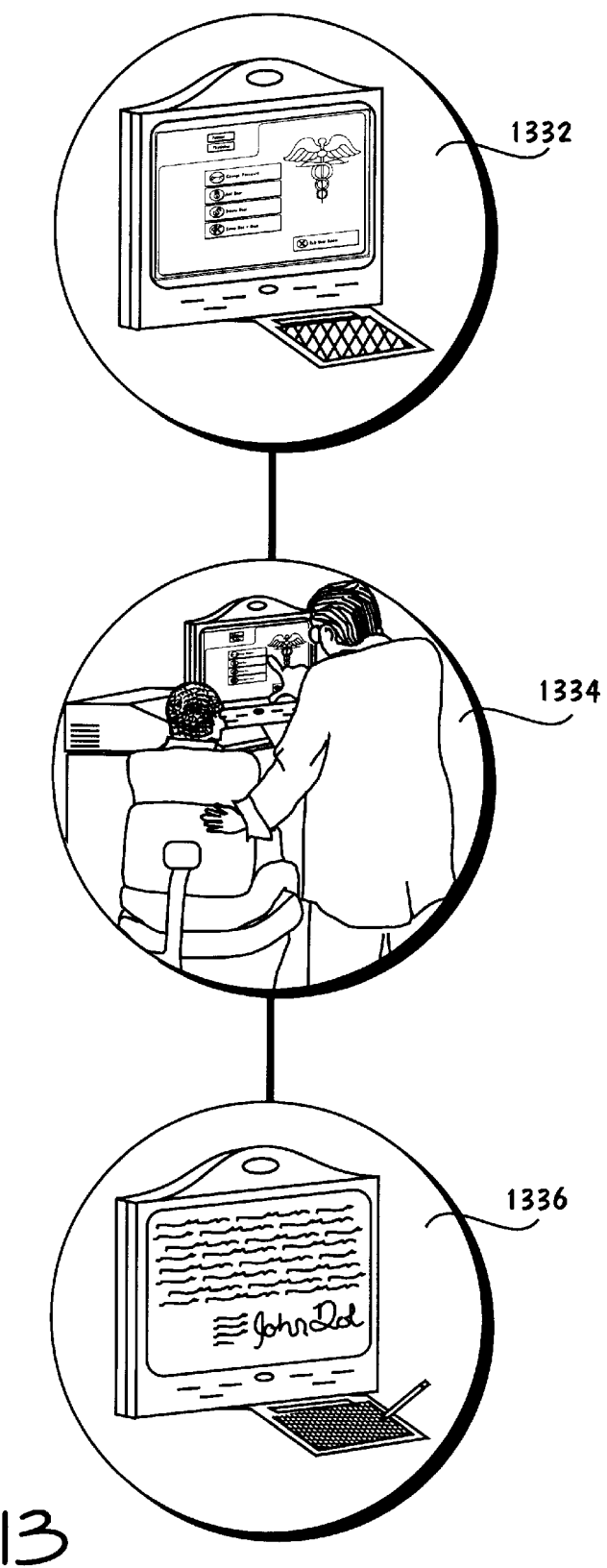
FIG. 13 is a diagram of a three-step interactive patient education and informed consent process using a VITAL Center of an embodiment.

FIG. 13 is a diagram of a three-step 1332–1336 interactive patient education and informed consent process using a VITAL Center of an embodiment. The goal of the VITAL Center is to provide an interactive patient education and informed consent process that reduces patient anxiety, increases patient comprehension and improves the level of personal interaction between patient and physician. The VITAL Center of an embodiment facilitates patient understanding of recommended procedures and reduces patient anxiety using presentations that offer information that has been physician peer reviewed as well as examined by leaders in patient education and legal experts to ensure that it is accurate, current, and comprehensive. The VITAL Center enhances the interaction between a patient and physician by establishing a foundation of knowledge that fosters a more meaningful patient-physician discussion about the procedure. After the VITAL Center presentation and physician consultation time, patients will have a comfortable understanding of the procedure and be able to offer their truly informed consent.

During the presentation step 1332, a patient watches and interacts with the VITAL Center presentation on a recommended procedure. The presentation offers a baseline education about the procedure including the associated risks, benefits and alternatives. The patient's comprehension of the material is confirmed throughout the presentation using summary questions focused on key information. The patient is encouraged to record their own questions or concerns about the procedure while watching the presentation.

After the presentation is finished, a healthcare professional returns to review the patient's recorded questions or concerns, at step 1334. Any information the patient did not understand is further explained at this time. This personal discussion is focused on reinforcing the information, reducing the patient's anxiety about the upcoming procedure and developing trust with the patient.

After all questions and concerns have been addressed and the patient has a comfortable understanding of the procedure, the patient is asked to sign an informed consent electronically, at step 1336. An acknowledgment of obtaining the informed consent will be printed from the VITAL Center to be included in the patient's file. Through digital video capture, the VITAL Center simultaneously records the information presented, the patient-physician interaction, and the informed consent process. The entire recorded education session and informed consent is stored permanently on optical disk media.

Figure 13A:
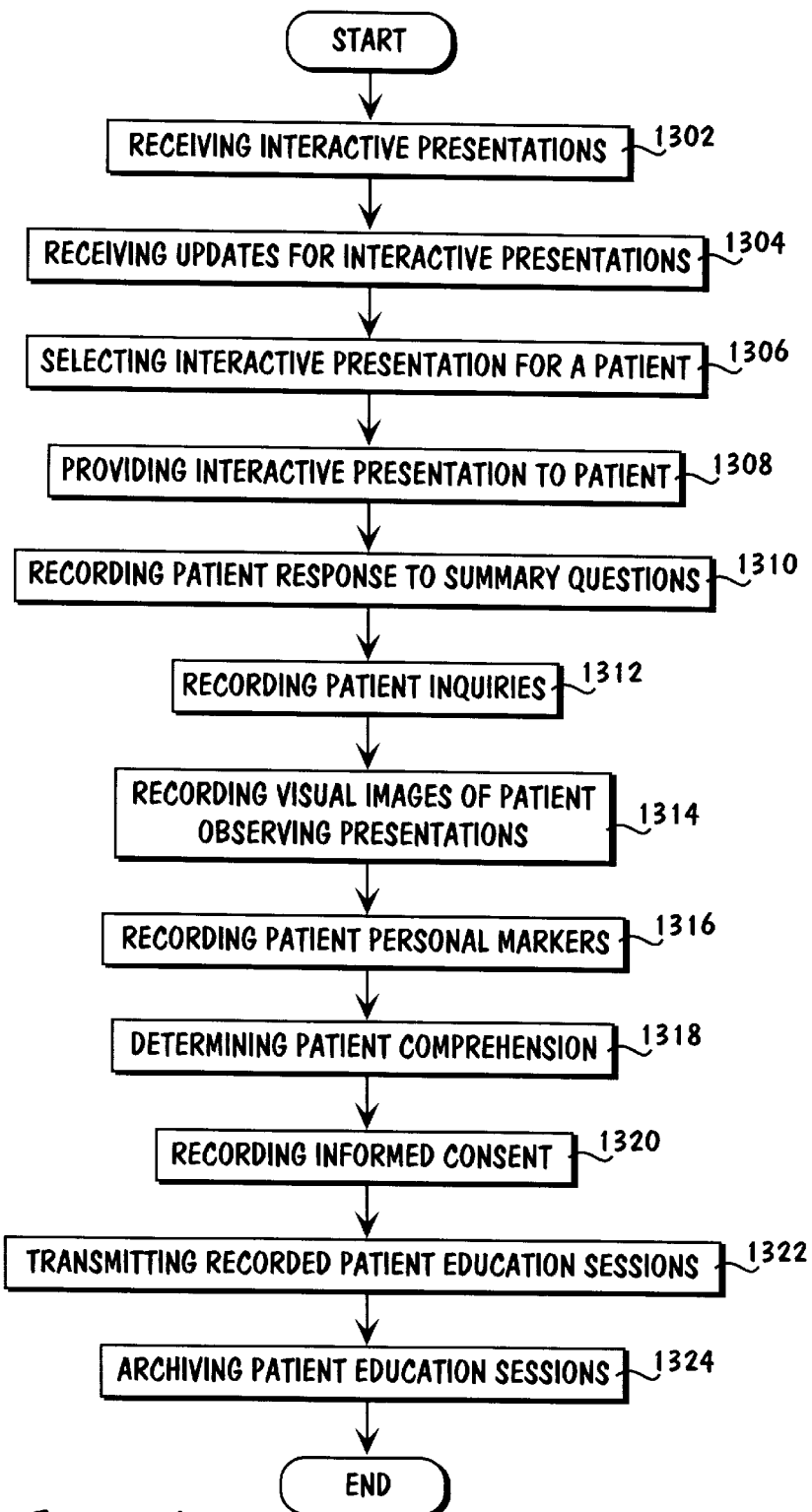
FIG. 13A is a flowchart of a method for obtaining informed patient consent of an embodiment.

FIG. 13A is a flowchart of a method for obtaining informed patient consent of an embodiment. Operation begins at step 1302, at which interactive presentations are received by the VITAL Center. Updated information is received for the interactive presentations, at step 1304. An interactive presentation is selected for a patient to view, at step 1306. This selection may be performed by a healthcare provider, but is not so limited. The selected interactive presentation is presented to the patient, at step 1308. The interactive presentation may include text, audio, animations, and video presentations, but is not so limited. During the interactive presentation, the VITAL Center records patient responses to summary questions, at step 1310, patient inquiries including questions, at step 1312, and visual images of the patient observing the interactive presentation, at step 1314. Furthermore, the VITAL Center may record patient personal markers including biological markers, at step 1316. The patient's comprehension of the presentation is determined, at step 1318. An informed patient consent is recorded, at step 1320, if it is determined that the patient comprehends the material presented during the interactive presentation. A recorded patient education session is transmitted by the VITAL Center to a data system or facility, at step 1322, wherein the patient education session includes the interactive presentation, the recorded visual images of the patient observing the presentation, the recorded patient responses, the patient inquiries, and recorded personal markers. The patient education sessions may be encrypted for transmission. The patient education sessions are stored and archived by the data system.

Figure 14:
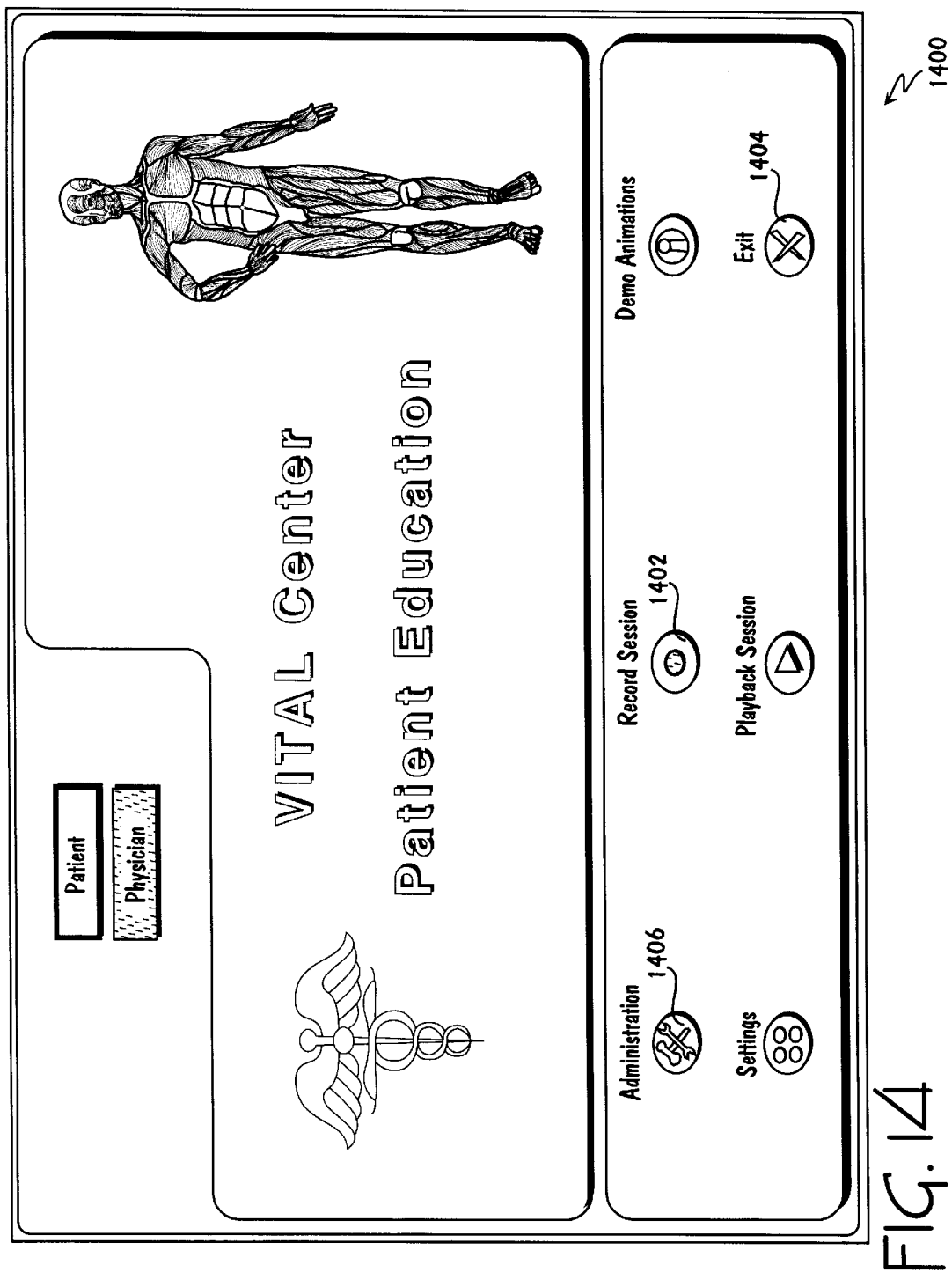
FIG. 14 is a Patient Education Screen of a VITAL Center of an embodiment.
Figure 15:
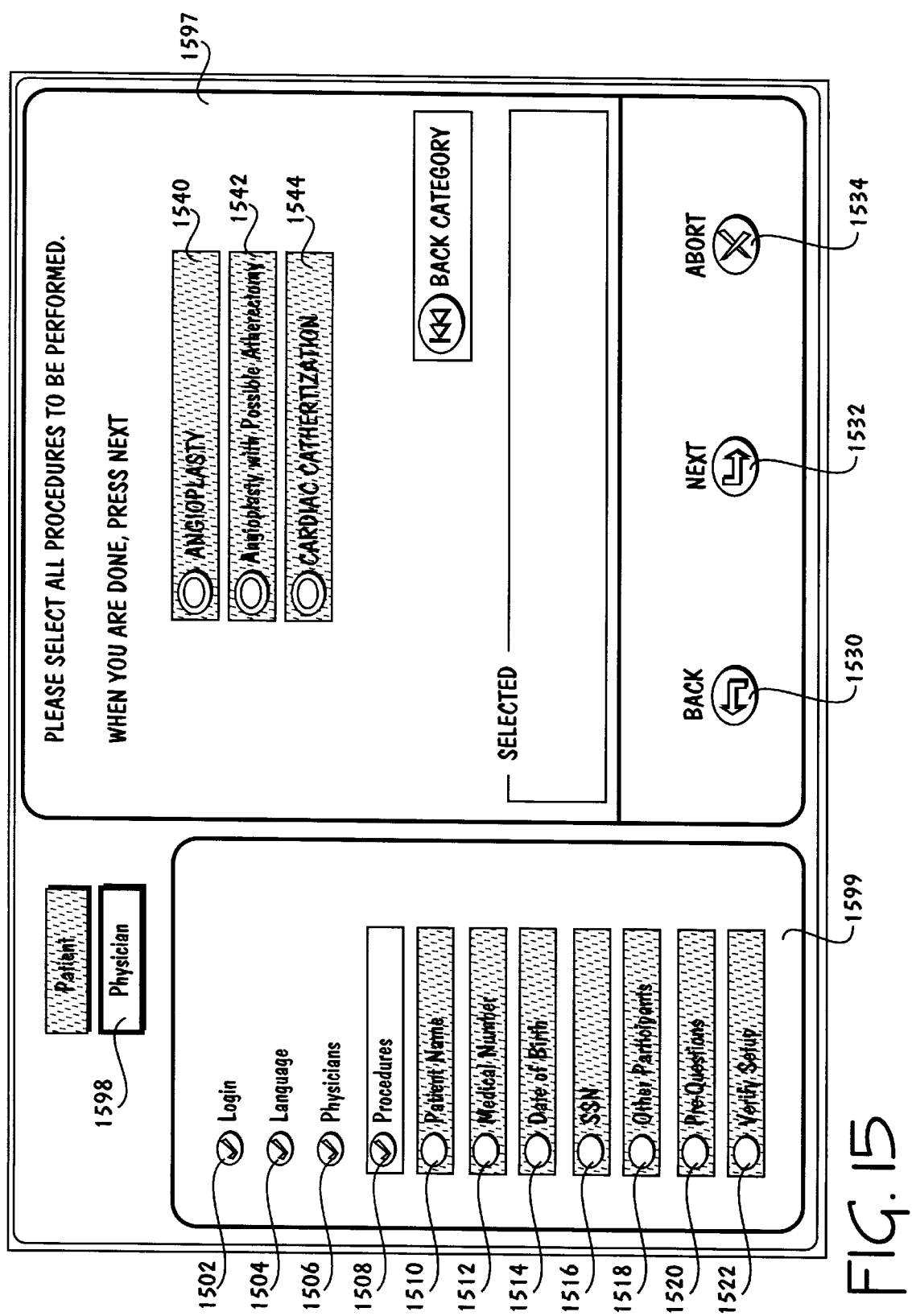
FIG. 15 is a divided screen of an embodiment for entry of patient information into a VITAL Center by a healthcare provider.

Operation of the VITAL Center of an embodiment in a patient education session begins by moving the portable VITAL Center to a suitable patient viewing area, turning on the VITAL Center, and following the prompts for a start-up procedure. Upon start up of the VITAL Center, a Patient Education Screen will be presented. FIG. 14 is a Patient Education Screen 1400 of a VITAL Center of an embodiment. To start the patient education session press the "Record Session" button 1402, whereupon the screen will divide and show a list of items required for entry with associated symbols, icons, or buttons. FIG. 15 is a divided screen 1500 of an embodiment for entry of patient information by a healthcare provider. While the list of items 1599 required for entry is displayed in a portion of the divided screen, another portion 1597 of the screen contains the information appropriate to the icon selected and any corresponding instructions. Along with the list of items 1599, an embodiment displays an on-screen keyboard (not shown) with which patient information is entered. This patient information is entered into the program by a healthcare provider in order to start the session. The highlighted "Physician" icon 1598 indicates that the items accessed using this screen may only be accessed by the healthcare provider. The healthcare provider may be a physician, a nurse, a technician, or any other qualified employee of the healthcare facility. This information may be entered prior to patient interaction.

The list of items 1599 of an embodiment provides indicators as to which items have been entered and which items remain to be entered. In the example shown, login 1502, patient language selection 1504, and physician selection 1506 have been completed as indicated by the presentation of checkmarks on the displayed icon. Selection of procedures 1508 is in progress as indicated by the highlighted icon. Patient name 1510, medical number 1512, date of birth 1514, Social Security number 1516, other participants 1518, pre-questions 1520, and verify setup 1522 remain to be entered as indicated by the absence of checkmarks on the displayed icons.

A number of buttons 1530–1534 are presented on the divided screen to assist in the entry of information, but the embodiment is not so limited. A "Next" button 1532 will move the presentation from one screen to the next. A "Back" button 1530 will move the presentation back to a previous screen. An "Abort" button 1534 will end the session and return the presentation to the "VITAL Center Patient Education" screen.

In preparing for a patient education session, entry of patient information proceeds with selection of the "Login" icon 1502, wherein an authorized physician is prompted for login information. Entry of login information in the form of a name and password is made using the keyboard of the divided screen, but is not so limited.

Following successful login of a physician, the "Language" icon 1504 is selected. Selection of the "Language" icon 1504 provides for the selection of the patient's language from a number of choices presented. This selection controls the language used for presenting the interactive presentation.

Selection of the "Physicians" icon 1506 provides for selection of the names of the physicians performing the procedure from a list presented. The selection of an embodiment is made by pressing an icon next to the name of the physicians, for example:

| O | Robert Clark MD | O | Michael Brown MD |
|---|---|---|---|
| O | Fred Jackson MD | O | Peter Black MD |

If the names of the physicians performing the procedure are not on the presented list, then names may be manually entered. To manually add a physician's name, a "Manual Add" icon is selected, and the physician's name and title (MD, DO) is inputted when prompted. The newly added name will appear among the pre-printed names, for example:

| O | Robert Clark MD | O | Michael Brown MD |
|---|---|---|---|
| O | Fred Jackson MD | O | Peter Black MD |
| O | John Hansen MD | | |

Following selection of the physicians, a procedure selection is initiated by selecting the "Procedures" icon 1508. In an embodiment, a number of procedures 1540–1544 may be presented. The procedure screen may move from very general to very specific until the desired procedure is identified. The following is an example of the screen changes seen when "Surgery" is the selected procedure:

| O | Anesthesia | | |
|---|---|---|---|
| O | Surgery (pressed) | | |
| O | Radiology | | |
| | Changes to the following screen | | |
| O | Integumentry System | O | Digestive System |
| O | Musculoskeletal System | O | Urinary System |
| O | Respiratory System | O | Laproscopic |
| O | Cardiovascular System (pressed) | O | Maternity |
| | Changes to the following screen | | |
| O | Percutaneous Transluminal Coronary Angioplasty | O | Cardiac Catheterization |
| O | Radiofrequency Catheter Ablation | O | PTCA with Rotational athrectomy |
| O | Cardiac catheterization (pressed) | | |

If an error is made and the wrong procedure is selected, then the button associated with that procedure is repressed and the procedure is unselected. The procedure selected will be displayed in the "selected box" at the lower left-hand area of the screen of an embodiment.

The patient's name is entered by selecting the "Patient Name" icon 1510. The on-screen keyboard (not shown) of an embodiment is used to enter the patient's name by touching the keypads presented on the screen. Alternately, a mouse or joystick may be used in combination with an on-screen cursor to select characters that spell the patient's name. In another embodiment, a speech recognition system component may be used that allows the physician to speak the patient's name or the letters of the patient's name. The patient's name is entered including first name, middle initial, last name, and suffix. An entry error is corrected using a backspace key. Following entry of the patient's name, the patient's medical record number, date of birth, and social security number are entered by selecting the "Medical Number" icon 1512, the "Date of Birth" icon 1514, and the "SSN" icon 1516, respectively.

If any individuals other than the patient will be present in the room during the presentation, their names should be entered into the system. Selection of the "Other Participants" icon 1518 allows for entry of the names of any participants that will be present during the presentation. Once the names are entered, press a displayed "Add" button and the names will appear in the "Participant's Box". If an error is made on entry, press a displayed "Clear Participants" button and the name will be removed from the screen. The relationship of the participant to the patient is entered by selecting a relationship from a presented list. If none of the options presented are applicable press a displayed "Manual Add" button and a keyboard will appear on the screen that allows for manual addition of the participant's relationship. The newly added category will appear among the previously printed options and will be highlighted with a "✓". For example:

| O | Husband | O | Father |
|---|---|---|---|
| O | Wife | O | Brother |
| O | Guardian | O | Sister |
| O | Mother | O | Son |
| | | ✓ | Significant Other |

A prompt is next presented from which a primary signer is selected for the informed consent. The primary signer is selected from the participants present by pressing the symbol or icon next to the appropriate name.

Any pre-existing conditions that are indicated in the patient's medical record are entered from a list provided on the screen upon selection of the "Pre-Questions" icon 1520. Upon indicating that a patient has no pre-existing conditions or completing entry of the pre-existing conditions, another screen is presented containing a list of drugs and medications. A selection is made from the list of all drugs and medications that are to be used during the procedure.

Figure 16:
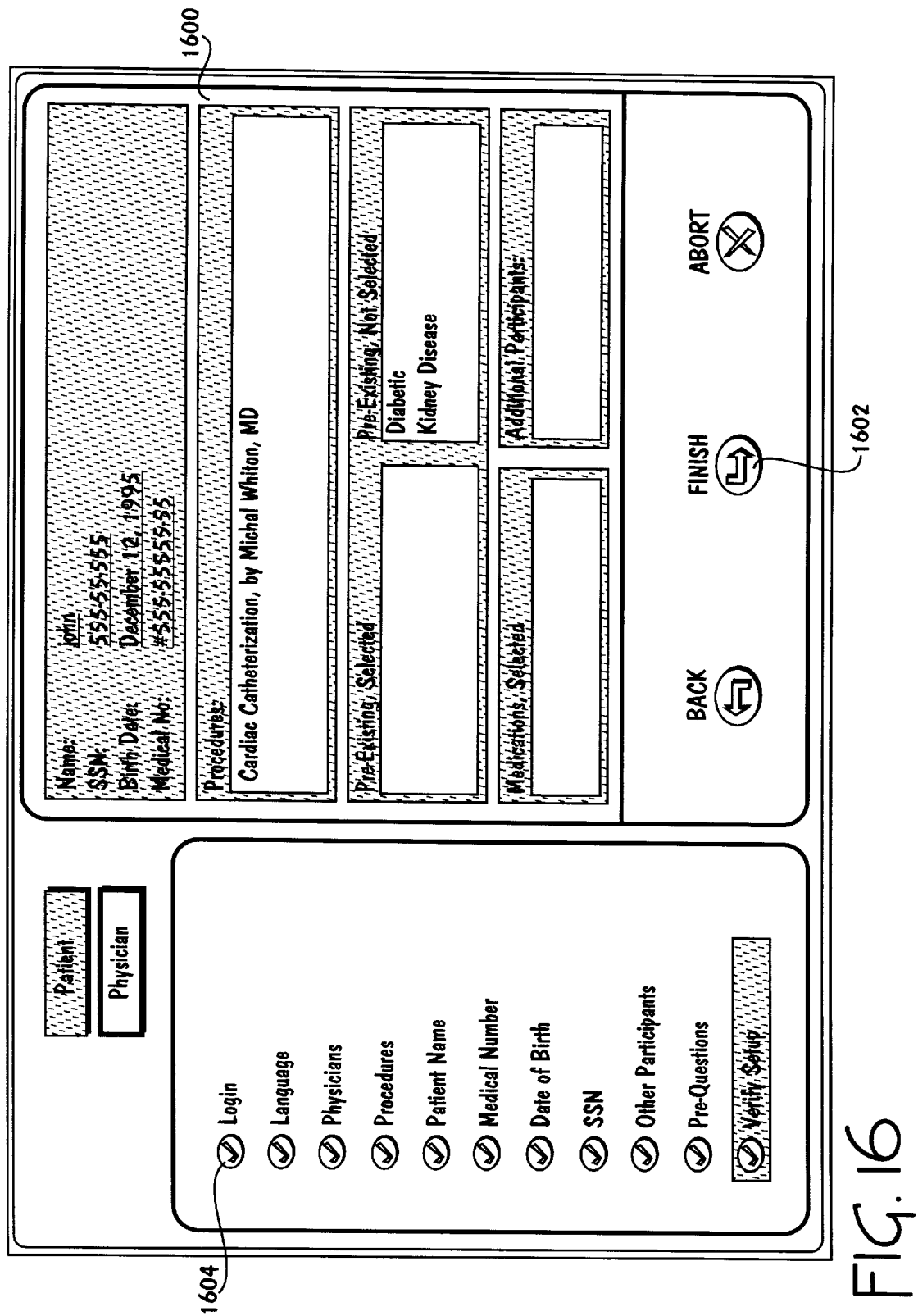
FIG. 16 is a physician verification screen of a VITAL Center of an embodiment.

Upon completing the entry of all aforementioned patient information using icons 1502–1520, a physician verification screen is selected for presentation using the "Verify Setup" icon 1522. FIG. 16 is a physician verification screen 1600 of a VITAL Center of an embodiment. The physician verification screen 1600 is used by the physician to verify correct entry of all patient information from the medical record. If all information is correct then the interactive procedure information is ready for presentation to the patient. If any errors are noted or an entry is to be modified, then the corresponding icon is reselected from the list 1599. Selection of the appropriate icon returns the presentation to the corresponding screen. Upon correction of the errors, the presentation is returned to the physician verification screen.

After entering and verifying all patient information, the patient is escorted to a viewing area containing the VITAL Center and introduced to the VITAL Center. An example introduction statement follows:

"Mrs. Jones, Dr.\_\_\_\_ has just talked with you about needing to have a \_\_\_\_. I am sure you have questions about the procedure and what will happen. Dr.\_\_\_\_ will be using The VITAL Center system, to provide you with the most up-to-date information regarding this procedure, its risks and benefits. The presentation will take about 30 to 45 minutes and at the end of the video presentation Dr.\_\_\_\_ will be in to answer any additional questions you may have."

Following the introduction, any patient questions about the VITAL Center are answered. When the patient is ready to begin viewing a presentation on a procedure, initiation of the patient session is started using a displayed "Finish" icon 1602.

Following the introduction, an animated patient tutorial giving a brief overview of how to use the touch screen is presented along with some basic information regarding the presentation. Typically, a representative of the health care provider will stay with the patient during the tutorial to answer any questions and to make sure that the patient is comfortable in using the VITAL Center. Patient use buttons presented include a pause button, a play button, a replay button, a question button, a done button, and a stop button. The "Pause" button pauses the presentation. The "Play" button restarts the presentation after it has been paused. The "Replay" button goes back to the beginning of the section that was being presented, and is used if the patient misses something or does not fully understand the first time. The "Question" button allows the patient to stop the presentation and ask a question. The question will be stored and retrieved at the end of the session by the physician to be reviewed. The "Done" buton is used, after a patient finishes asking a question, to restart the presentation. The "Stop" button ends the session at anytime.

Upon completion of the tutorial, a patient verification screen will appear from which all entered data is verified by the patient. FIG. 17 is a patient verification screen 1700 of a VITAL Center of an embodiment. The highlighted "Patient" icon 1799 indicates that this is the screen used by the patient for verification of the patient information. The patient verification screen 1700 comprises a number of sections, including Patient Information 1710, Patient Has 1720, Medications 1730, Additional People 1740, Does Not Have 1750, Procedures 1760, and Verification 1770. The patient or guardian is informed that the basic information from their medical records has previously been entered and that they are now to verify the spelling of their name 1711, birth date 1712, Social Security number 1713, procedure 1760, and physician name 1761 prior to beginning the presentation. The patient information is reviewed with the patient for completeness and accuracy. Following provision of the instructions and patient verification that the information is correct, the patient should select the "Agree" button 1771.

If some of the information is incorrect the patient should select the "Disagree" button 1772. Selection of the Disagree button will return the presentation back to the physician verification screen 1600, where the information can be corrected by the attending healthcare professional. The left-hand side of the physician verification screen 1600 will display a list 1604 of specific set-up screens. A specific screen is selected for modification from the list 1604 by touching the symbol or icon next to the name of the screen. The presentation program will revert back to that screen. Upon completion of all corrections, the displayed "Next" button is selected and the presentation is returned to the patient verification screen 1700. The patient is again instructed to review the corrected patient information for completeness and accuracy. Following patient verification of the patient information, the patient should select the "Agree" button 1771 to continue the presentation.

Upon selection of the "Agree" button 1771 by the patient, a screen is presented that informs the patient that the session is being recorded for quality assurance and record keeping purposes. By selecting a displayed "OK" button in the middle of the screen, the patient gives their permission to be recorded and allows the presentation to proceed.

Figure 18:
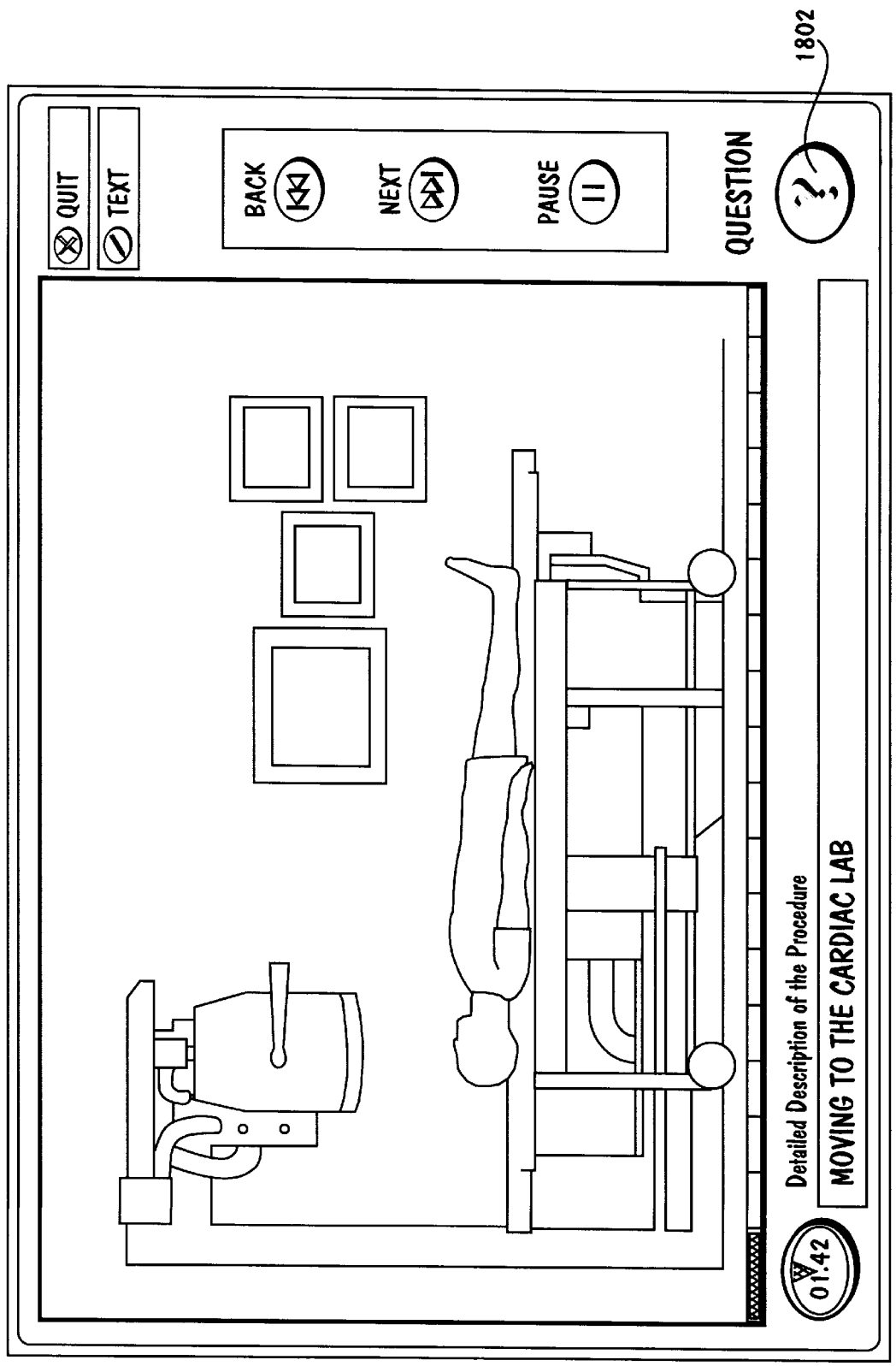
FIG. 18 is a scene from a VITAL Center presentation of an embodiment.
Figure 19:
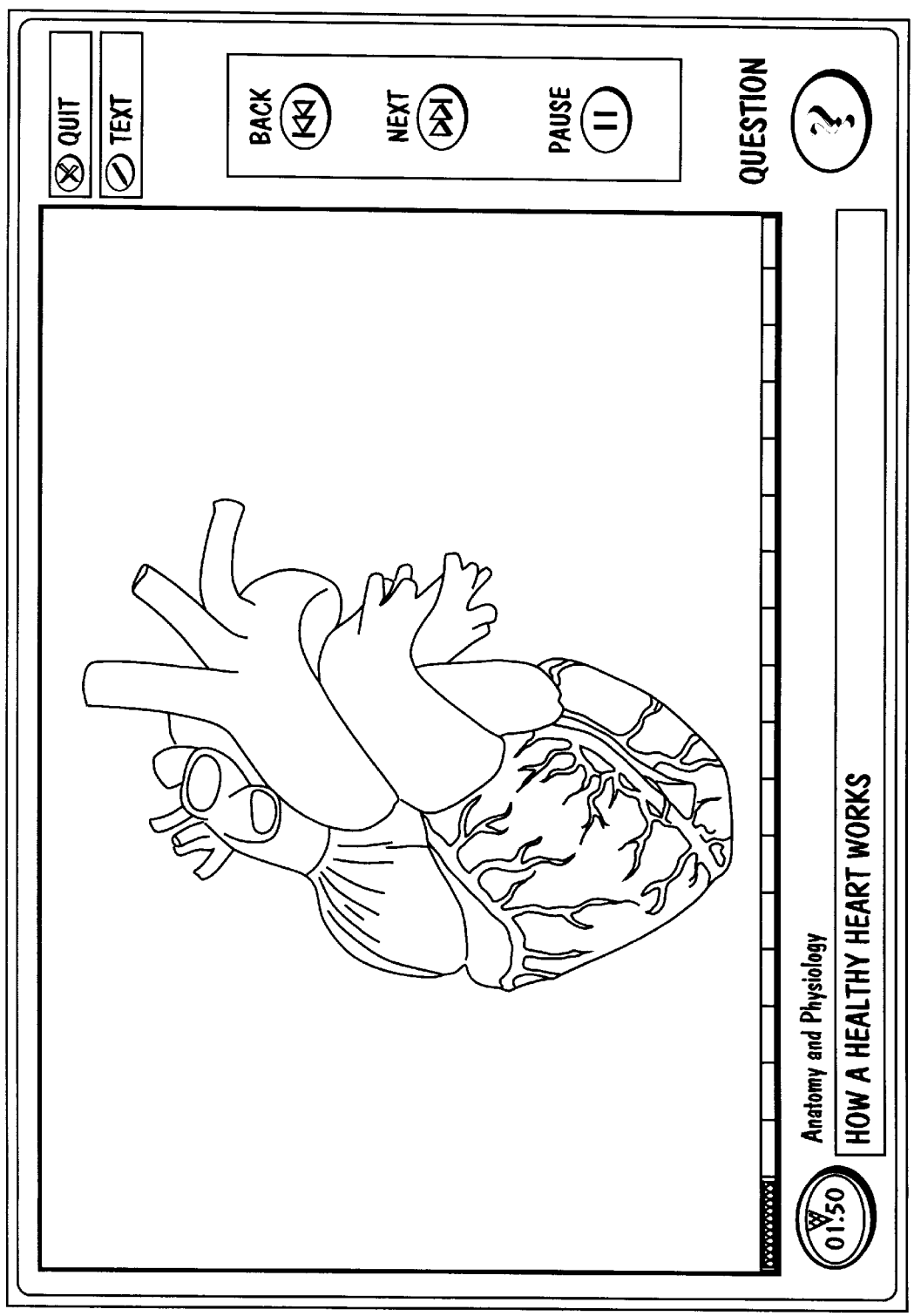
FIG. 19 is another scene from a VITAL Center presentation of an embodiment.

The presentation comprises predefined and recorded information that is presented to the patient using audio, video, animation, and other visual methods on the VITAL Center screen. FIG. 18 is a scene from a VITAL Center presentation of an embodiment. FIG. 19 is another scene from a VITAL Center presentation of an embodiment. The presentation information is stored in a database of segments that are organized for each patient session according to preexisting conditions of the patient, native language of the patient, type of procedure for which the patient has been recommended, or prescribed pharmaceuticals. This organization is defined by the information entered by the healthcare provider in the initial demographic prompt screens, but is not so limited.

Figure 20:
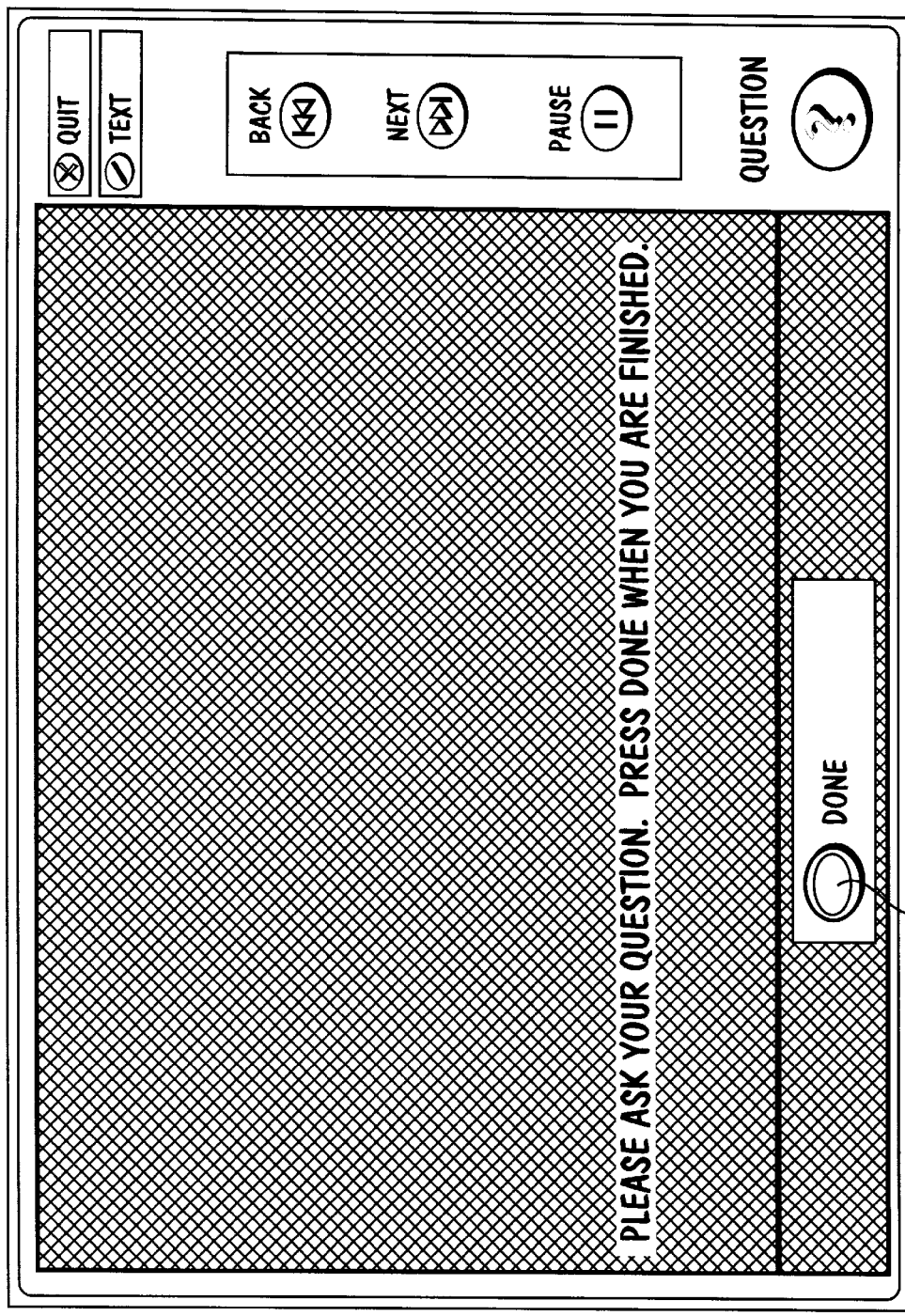
FIG. 20 is a screen presentation during a patient question of a VITAL Center of an embodiment.

Throughout the presentation, the patient may ask specific questions for the attending physician. The patient initiates the questions by selecting the "Question" icon 1802 on the presentation screen. The selection pauses the presentation and records the patient asking the question. FIG. 20 is a screen presentation during a patient question of a VITAL Center of an embodiment. When the patient is finished asking a question, they select a "Done" icon 2002 and the presentation resumes.

Figure 21:
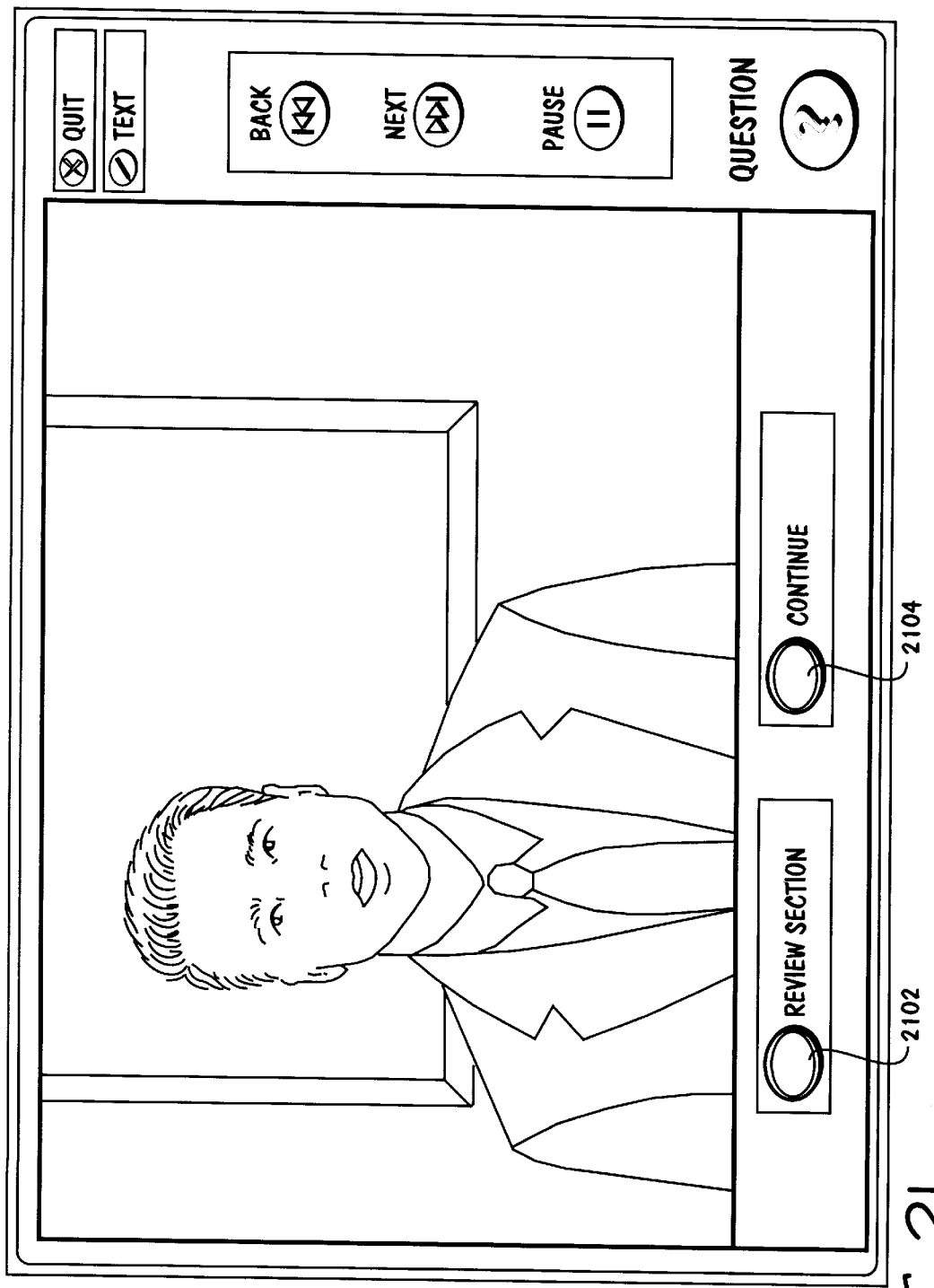
FIG. 21 is a screen presentation at a review option point of a VITAL Center of an embodiment.

The presentation sessions of an embodiment include points where the patient is allowed to review a section or continue. FIG. 21 is a screen presentation at a review option point of a VITAL Center of an embodiment. Selection of the "Review Section" icon 2102 causes the VITAL Center to replay the corresponding section of the presentation. Selection of the "Continue" icon 2104 causes the VITAL Center to continue the presentation with the next scheduled section.

Figure 22:
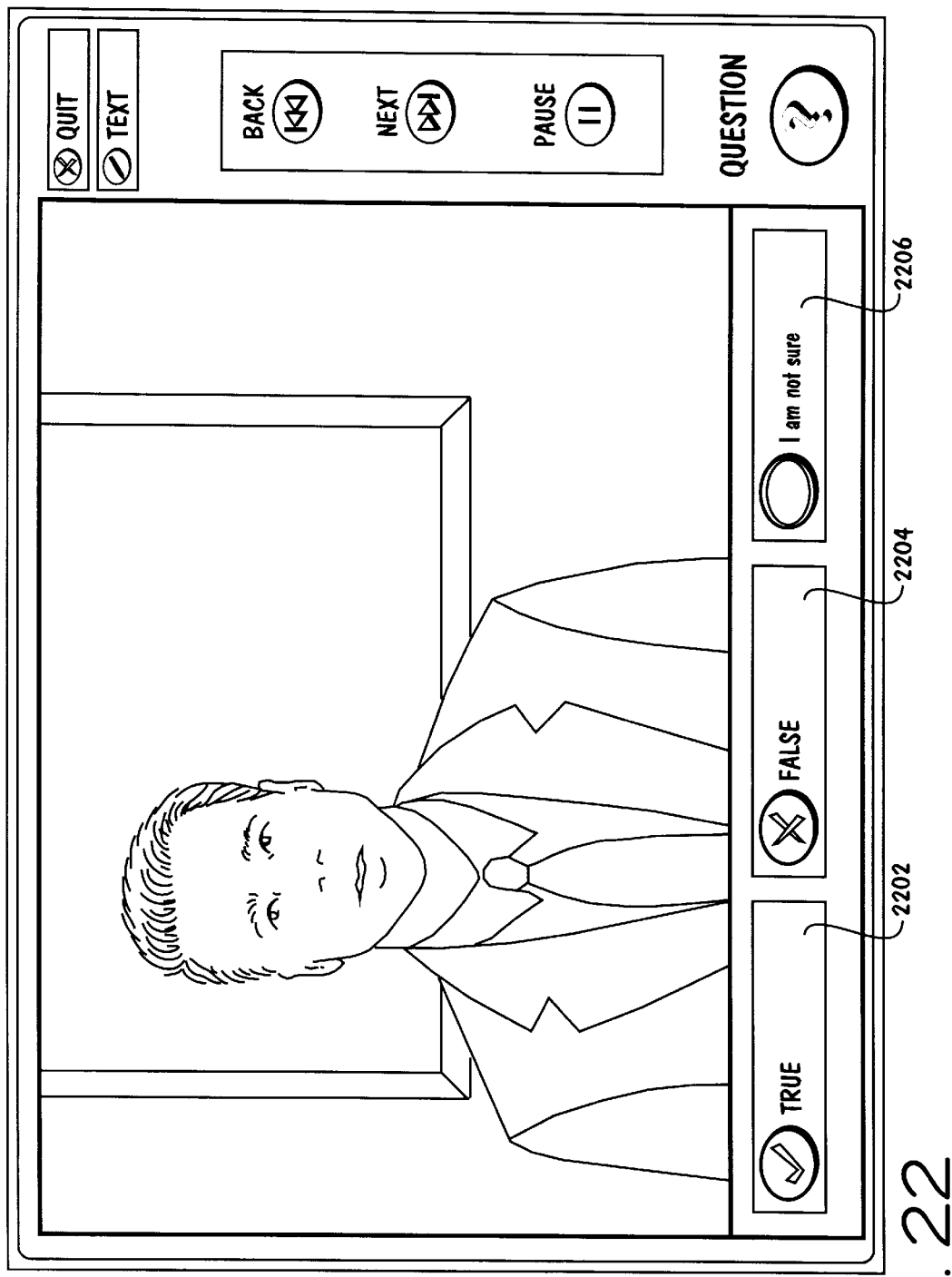
FIG. 22 is a screen presentation accompanying a summary question of a VITAL Center of an embodiment.

The presentation sessions of an embodiment include a number of segments that often end with summary questions to which the patient must respond. The patient answers to the summary questions are used to determine patient comprehension of the information presented. FIG. 22 is a screen presentation accompanying a summary question of a VITAL Center of an embodiment. The answer icons 2202–2204 presented are appropriate to the corresponding summary question. In this example, the summary question is of the True/False type. Selection of the "True" icon 2202 registers a patient answer of "True" to the corresponding summary question, while selection of the "False" icon 2204 registers a patient answer of "False" to the corresponding summary question. Selection of the "I am not sure" icon 2206 indicates the patient does not know the answer to the summary question, and may cause the VITAL Center to replay the appropriate portion of the presentation.

Upon completion of the educational portion of the presentation, a summary screen (not shown) is presented at the bottom of the video screen which will allow the patient to choose from one of three buttons. The three buttons of an embodiment include a "Review Sections" button, a "Frequently Asked Questions" (FAQ) button, and a "Done" button. The "Review Sections" button provides a screen showing a complete list of presentation segments from which the patient can choose. By selecting the button or icon next to a listed segment, the patient will be able to review that segment. Upon completion of the section review, the display returns to the summary screen. The "FAQ" button provides a list of frequently asked questions regarding the procedure, along with the answers to those questions. The "Done" button is selected when the patient is ready to have the physician review their questions and to discuss the procedure. When the Done button is selected in an embodiment, the monitor will change to a waiting screen that will display a message instructing the patient to notify the healthcare provider that they have completed this segment of the session.

Figure 23:
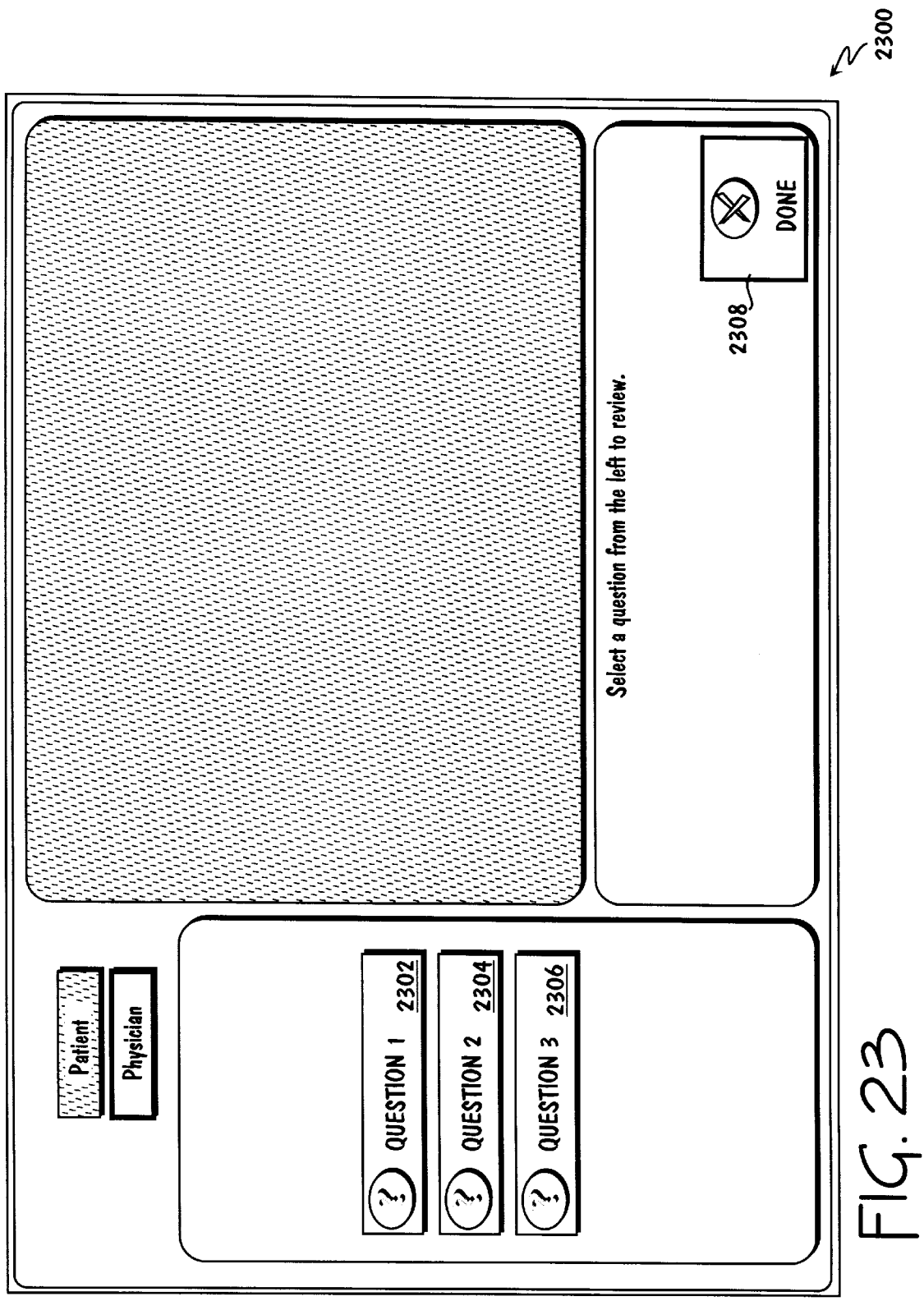
FIG. 23 is a Question Review screen of a VITAL Center of an embodiment.

The attending physician begins review of any patient-generated questions by entering their name and password into the VITAL Center. If the patient has asked questions during the presentation a Question Review screen 2300 is presented. FIG. 23 is a Question Review screen 2300 of a VITAL Center of an embodiment.

A number of blocks 2302–2306 will be presented corresponding to the number of questions generated by the patient. The patient's particular questions are accessed by selecting the block containing the corresponding question number. For example, the Question Review Screen 2300 indicates that the patient generated three questions during a patient education session. Selection of the Question 1 block 2302 initiates the visual and audio playback of the patient's first question. Selection of the Question 2 block 2304 initiates the visual and audio playback of the patient's second question. Selection of the Question 3 block 2306 initiates the visual and audio playback of the patient's third question.

Once all patient questions have been reviewed and discussed by the attending physician, and the patient has no further questions regarding the procedure, the "Done" button 2308 is selected. Selection of the "Done" button 2308 results in presentation of an Informed Consent signature screen.

FIG. 24 is an Informed Consent signature screen 2400 of a VITAL Center of an embodiment. The patient is instructed to sign their signature on an electronic pad if they consent to having the presented procedure performed and agree with the terms of the consent form 2402. The patient signature 2499 is displayed on the signature screen 2400. If the patient is dissatisfied with how their signature 2499 looks they may select the "Clear" icon 2404 to remove the signature, wherein they may resign the electronic pad. When satisfied with their signature, the patient should select the "Done" icon 2406. A "Not Ready to Sign" icon 2408 is presented for selection when the patient is not ready to consent.

Figure 25:
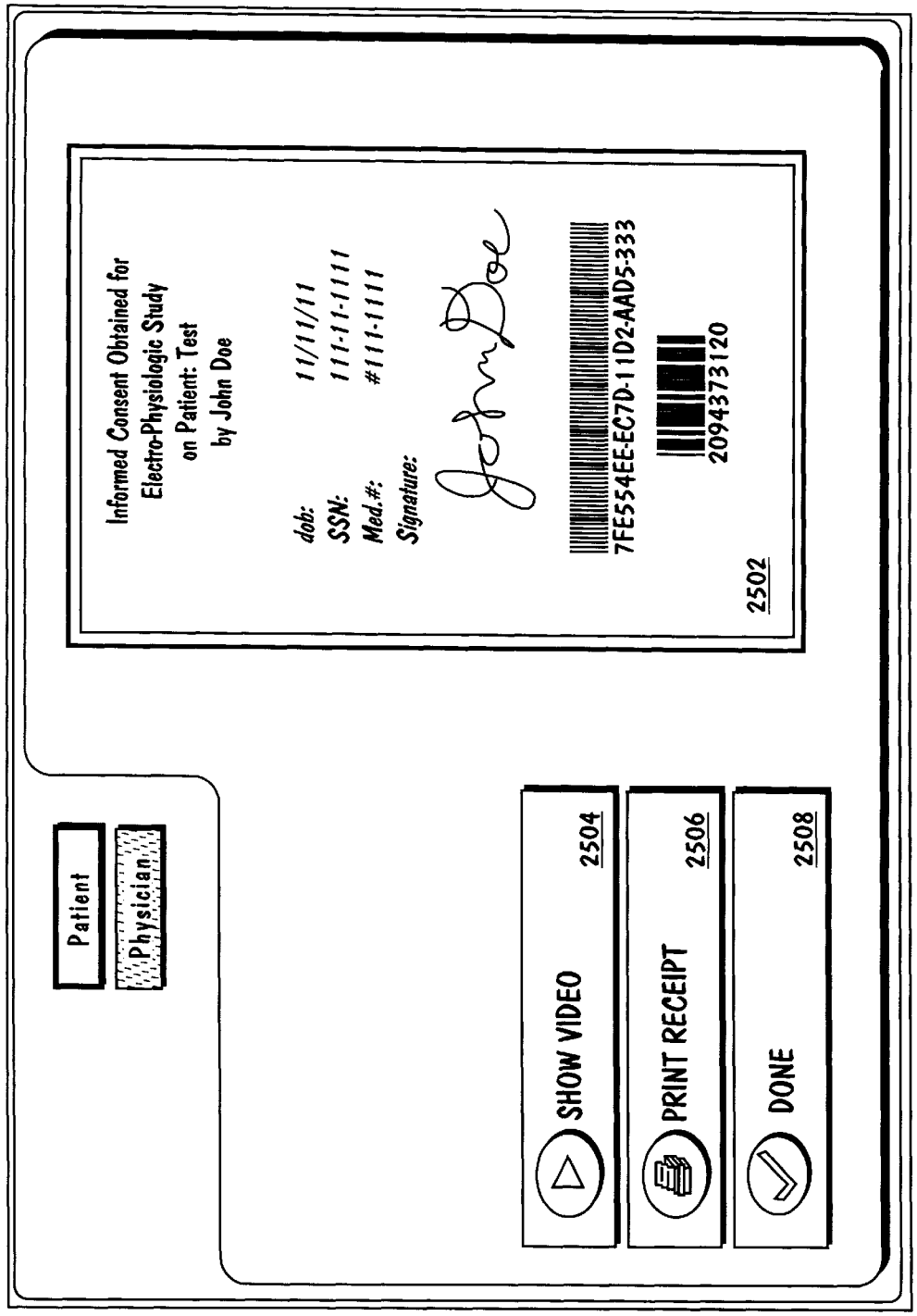
FIG. 25 is a Consent Obtained screen of a VITAL Center of an embodiment.

Upon signing the signature screen and selecting the "Done" icon 2406, the VITAL Center of an embodiment displays a Consent Obtained screen. FIG. 25 is a Consent Obtained screen 2500 of a VITAL Center of an embodiment. This screen 2500 presents a form 2502 that includes the patient's signature to the consent along with the patient's identifying information and associated barcode information. The Consent Obtained screen 2500 includes a "Show Video" icon 2504, a "Print Receipt" icon 2506, and a "Done" icon 2508.

Selection of the "Print Receipt" icon 2506 causes a receipt to be printed that is used to verify that the patient has signed their informed consent and has completed the education session. The receipt may include the procedure, patient's name, physician's name performing the procedure, date of birth, Social Security number, medical record number, time, date, patient signature, and identification information. This receipt is to be placed on the patient's chart. The "Done" button is selected after the receipt is printed and results in the screen returning to the "VITAL Center Patient Education" screen 1400, from which a new session may be started.

Figure 26:
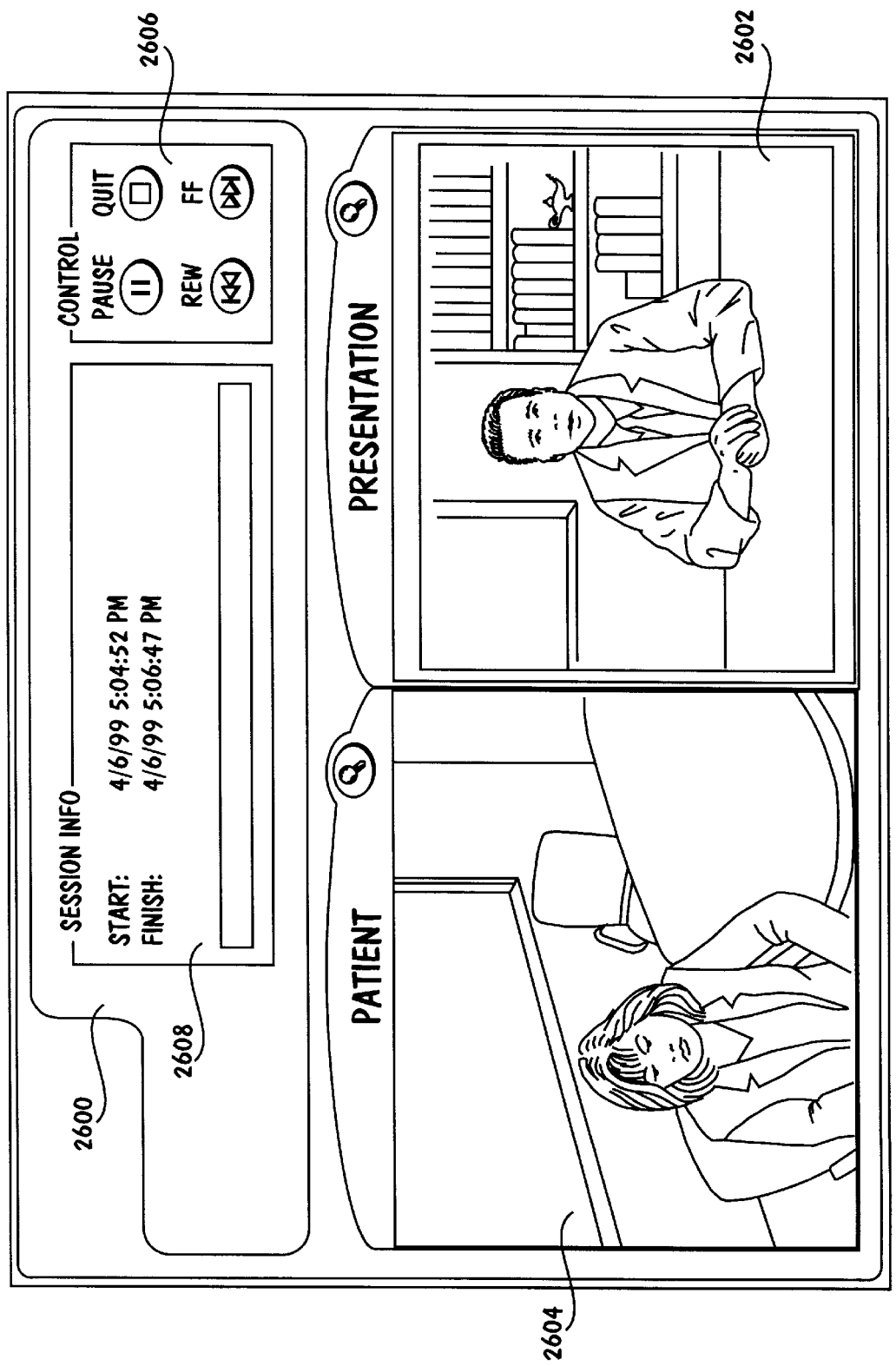
FIG. 26 is a replay screen of a VITAL Center of an embodiment.

Selecting the "Show Video" icon 2504 results in a replay of the patient education session. FIG. 26 is a replay screen 2600 of a VITAL Center of an embodiment. The replay screen 2600 simultaneously presents the interactive presentation 2602 as correlated with the visual images 2604 of the patient viewing the interactive presentation. The replay screen 2600 may be presented using a vertical split screen format, a horizontal split screen format, or a picture-in-picture format, but is not so limited. The replay screen 2600 may also include a control panel 2606 for controlling the replay as well as session information 2608 comprising date, timing, and position information.

The VITAL Center of an embodiment allows for the uploading of recorded patient education sessions and other medical information to a data system or facility. The VITAL Center also supports downloading of information from the data system. This upload/download is performed by accessing a network. The network may be a network dedicated to the VITAL Center system. Furthermore, the network may include local area networks (LANs), wide-area networks (WANs), and any combination of LANs and WANs. The network may also include the Internet. Moreover, the upload/download may be accomplished using a wireless network. During the uploading/downloading process, a message is presented to inform the operator that information is being uploaded to or downloaded from the data system. Once the upload/download process is complete, a message is presented to inform the operator that the process is complete.

Figure 27:
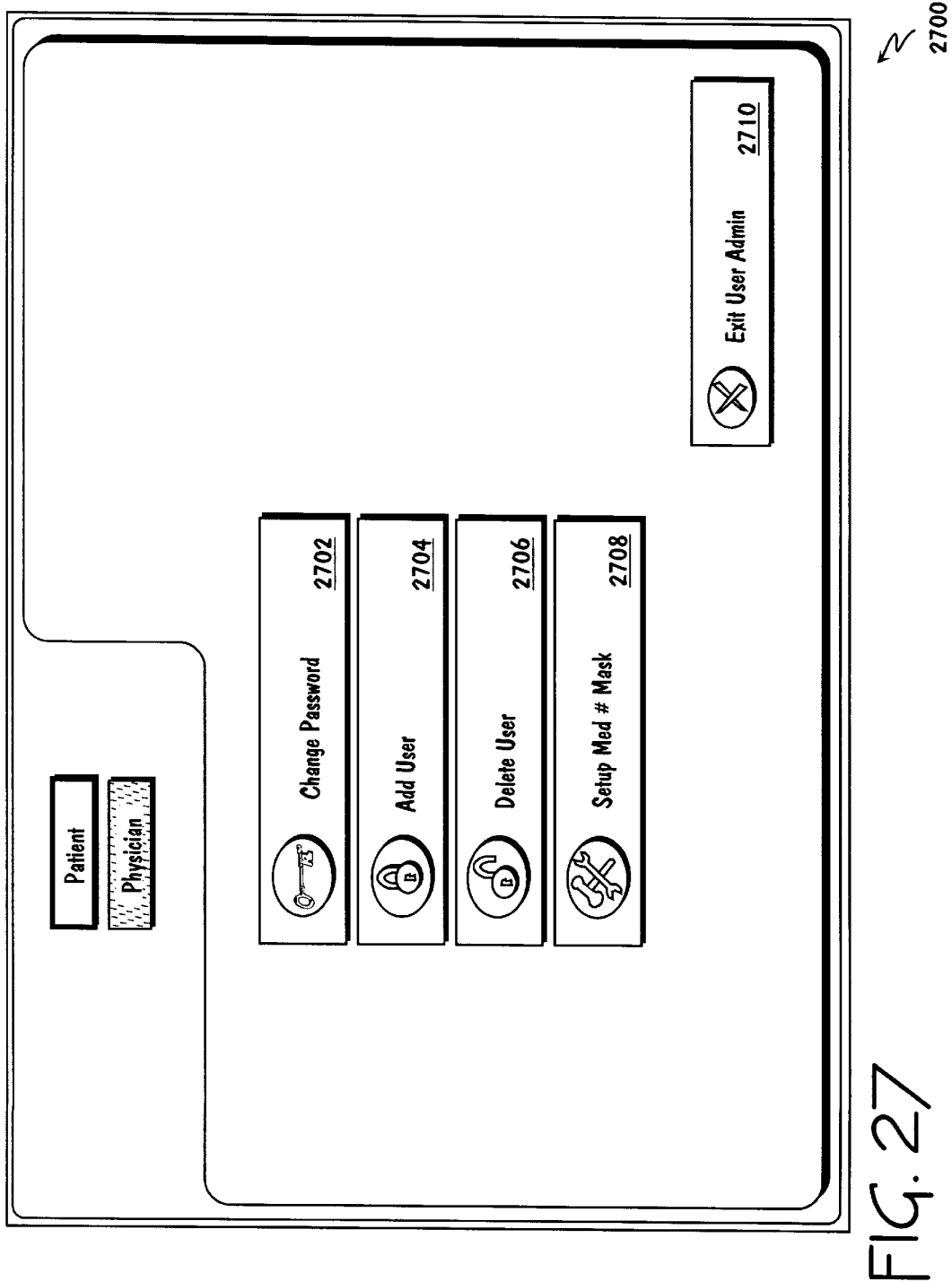
FIG. 27 is a User Administration screen of a VITAL Center of an embodiment.

A user administration function is provided in an embodiment that provides for changing passwords, adding users including doctors, deleting users including doctors, and setting up masks. FIG. 27 is a User Administration screen 2700 of a VITAL Center of an embodiment. The User Administration screen 2700 is accessed by selecting the "User Administration" button 1406 of the Patient Education screen 1400. The user enters the system by entering their name and password when prompted.

Password changes are initiated with the User Administration screen 2700 by selecting the "Change Password" button 2702. A screen (not shown) with a keypad and two password fields is presented. After entering a new password, a "Confirm Password" field is selected.

The password is entered a second time, for verification purposes. The "Done" button is selected following the second entry of the password.

Addition of a user is initiated from the User Administration screen 2700 by selecting the "Add User" button 2704. A screen and a keypad (not shown) are presented, and prompts are provided for information including a name, username, password, and password confirmation. A user type is also selected from one of a Session User, Physician, and Administrator. A Session User is allowed to log in to help patients through a session. A Physician is a session user, and will show up as one of the physicians during setup or a procedure. An Administrator may add and remove users. When all fields have been completed and the two password fields match, the "Done" button is selected. If the "Done" button is not enabled, there is either a blank field or the passwords do not match. Deleting a user is initiated from the User Administration screen 2700 by selecting the "Delete User" button 2706. A screen (not shown) is presented listing all usernames for the particular VITAL Center. The username corresponding to the user to be deleted is selected, and the "Delete" button is selected. The "Exit User Administration" button 2710 on the User Administration screen 2700 is selected in order to exit the user administration function.

Selection of the "Exit" button 1404 on the Patient Education screen 1400 initiates a shutdown of the VITAL Center. Upon entry of a user name and password, the screen will present two prompts:

| | | |
|---|---|---|
| O | Start Vital Center | |
| O | Shutdown | Press O shutdown |

Selection of the icon or symbol associated with "Shutdown" will cause the screen to momentarily go blank. A message indicating that it is safe to shutdown the VITAL Center will then be presented, at which time the VITAL Center may be turned off.

Although the invention has been described in terms of preferred embodiments, it will be understood that numerous variations and modifications may be made without departing from the spirit and scope of the present invention as described above and as set forth in the accompanying claims.

What is claimed is:

1. A method for obtaining informed patient consent, comprising:
   providing at least one interactive presentation on a medical procedure;
   recording patient response to at least one summary question of the at least one interactive presentation;
   recording at least one inquiry of the patient during the at least one interactive presentation;
   recording visual images of the patient observing the at least one interactive presentation;
   determining patient comprehension using the patient response; and
   recording an informed consent including an electronic signature of the patient.

2. The method of claim 1, further comprising:
   transmitting at least one recorded patient education session to a data system, wherein the at least one recorded patient education session includes the at least one interactive presentation, the at least one summary question, the recorded patient response, the recorded inquiry, the recorded visual images, the recorded personal marker, and the recorded electronic signature;
   receiving the at least one recorded patient education session; and
   archiving the at least one recorded patient education session, wherein archiving comprises storing the at least one patient education session on an optical disk storage media.

3. The method of claim 2, further comprising:
   receiving at least one update to the at least one interactive presentation from the data system, wherein the at least one update includes information selected from a group comprising new procedures, pharmaceuticals, statistics, and modifications to the at least one interactive presentation; and
   updating the at least one interactive presentation.

4. The method of claim 2, further comprising encrypting the at least one recorded patient education session for transmission, wherein transmitting and receiving are performed over a medium selected from a group comprising bidirectional networks, wireless networks, and the Internet.

5. The method of claim 1, further comprising:
   receiving a transmission including the at least one interactive presentation from a data system; and
   selecting the at least one interactive presentation to provide to the patient.

6. The method of claim 1, wherein the medical procedure is selected from a group comprising surgical procedures, non-surgical procedures, therapies, procedures involving chemicals and drugs, and testing.

7. The method of claim 1, wherein determining patient comprehension comprises:
   determining at least one score for at least one portion of the at least one interactive presentation using the recorded patient responses;
   determining a status of the at least one score using a specified threshold;
   when the at least one score is below the specified threshold, performing at least one action selected from a group comprising repeating the at least one interactive presentation, repeating at least one portion of the at least one interactive presentation, presenting information to supplement the at least one interactive presentation, readministering the at least one summary question, administering at least one additional summary question, and terminating the at least one interactive presentation.

8. The method of claim 1, wherein providing at least one interactive presentation comprises providing a presentation including at least one format selected from a group comprising audio, visual, audiovisual, closed circuit, and digital imaging, wherein the at least one interactive presentation is provided to the patient using a device selected from a group comprising hand-held devices, portable devices, and remote devices.

9. The method of claim 1, further comprising recording at least one personal marker of the patient, the at least one personal marker comprising at least one biological marker selected from a group comprising pulse rates, breath rates, blood pressure, fingerprints, toe prints, footprints, corneal scans, and retinal scans.

10. The method of claim 1, further comprising correlating the at least one interactive presentation with at least one of the recorded visual images of the patient observing the at least one interactive presentation, the recorded patient responses, and the recorded at least one inquiry, wherein the correlation allows for simultaneous observation during presentation of a visual record of a patient education session.

11. A system for obtaining informed patient consent, comprising:
    a processor-based remote audiovisual device for presenting at least one interactive presentation on a medical procedure, wherein the audiovisual device records at least one patient education session comprising recording visual images of a patient observing the at least one interactive presentation and recording an informed consent of the patient;
    a means for providing the at least one interactive presentation to the audiovisual device;
    a means for updating the at least one interactive presentation stored in the audiovisual device; and
    a means for storing and archiving the at least one patient education session.

12. The system of claim 11, wherein the means for providing and the means for updating the at least one interactive presentation comprises a data system that transmits the at least one interactive presentation and at least one interactive presentation update to the remote device, wherein the at least one update is selected from a group comprising new procedures, pharmaceuticals, statistics, and modifications to the at least one interactive presentation.

13. The system of claim 11, further comprising:
    a means for recording at least one personal marker of the patient;

a means for encrypting the at least one recorded patient education session;

a means for determining patient comprehension of the at least one interactive presentation;

a means for transmitting the at least one recorded patient education session to a data system; and a means for correlating the at least one interactive presentation with the at least one recorded patient education session.

14. The system of claim 11, wherein the at least one recorded patient education session further comprises the at least one interactive presentation, at least one summary question, a patient response to the at least one summary question, at least one inquiry of the patient, at least one personal marker of the patient, and a recorded electronic signature.

15. A system for obtaining informed patient consent, comprising:

at least one portable device coupled to a network, wherein each portable device includes at least one processor configured to:

provide at least one interactive presentation on a medical procedure, wherein the at least one interactive presentation includes at least one summary question;

record visual images of the patient observing the at least one interactive presentation;

determine patient comprehension of the medical procedure using a recorded patient response to the at least one summary question;

record the informed patient consent; and at least one data system coupled to the network, wherein each data system is capable of receiving and archiving at least one recorded patient education session from the at least one portable device, the at least one recorded patient education session including the at least one interactive presentation, the recorded visual images, and the recorded informed patient consent; and transmitting at least one update to the at least one interactive presentation, wherein the at least one update includes information selected from a group comprising new procedures, pharmaceuticals, statistics, and modifications to the at least one interactive presentation.

16. The system of claim 15, wherein each portable device is further configured to:

receive a transmission including the at least one interactive presentation from the at least one data system;

receive at least one update to the at least one interactive presentation from the at least one data system, wherein the at least one update includes information selected from a group comprising new procedures, pharmaceuticals, statistics, and modifications to the at least one interactive presentation; and update the at least one interactive presentation.

17. The system of claim 15, wherein each portable device is further configured to:

record at least one personal marker of the patient comprising at least one biological marker selected from a group comprising pulse rates, breath rates, blood pressure, fingerprints, toe prints, footprints, corneal scans, and retinal scans;

encrypt the at least one recorded patient education session for transmission; and transmit the at least one recorded patient education session to the at least one data system, wherein transmitting is performed over a medium selected from a group comprising bidirectional networks, wireless networks, and the Internet, wherein the at least one recorded patient education session includes the at least one interactive presentation, the at least one summary question, the recorded patient response, the recorded inquiry, the recorded visual images, a recorded personal marker of the patient, and the recorded electronic signature.

18. The system of claim 15, wherein each portable device is further configured to:

correlate the at least one interactive presentation with at least one of the recorded visual images of the patient observing the at least one interactive presentation, the recorded patient responses, the recorded at least one inquiry, and the recorded informed consent, wherein the correlation allows for simultaneous observation during presentation of a visual record of a patient education session; and replay the at least one recorded patient education session.

19. The system of claim 15, wherein each portable device further includes:

at least one display comprising a touch-sensitive screen through which the patient may enter information; and a visual image capture device that records the visual images, the visual image capture device selected from a group comprising a digital camera, a digital video camera, and a video camera.

20. The system of claim 15, wherein the at least one data system is further capable of:

transmitting the at least one interactive presentation to each portable device;

encrypting the at least one interactive presentation and the at least one update;

correlating the at least one interactive presentation with at least one of the recorded visual images of the patient observing the at least one interactive presentation, the recorded patient responses, and the recorded at least one inquiry, wherein the correlation allows for simultaneous observation during presentation of a visual record of a patient education session; and storing the at least one patient education session using an optical disk system.

21. A remote device for obtaining informed patient consent, comprising at least one processor, at least one memory, at least one display, and at least one input device, wherein the remote device is capable of providing at least one interactive presentation on a medical procedure;

recording patient response to at least one summary question of the at least one interactive presentation;

recording at least one inquiry of the patient during the at least one interactive presentation;

recording visual images of the patient observing the at least one interactive presentation;

determining patient comprehension using the patient response; and recording an informed consent including an electronic signature of the patient.

22. The remote device of claim 21, wherein the remote device is further capable of:

receiving a transmission including the at least one interactive presentation from a data system;

receiving at least one update to the at least one interactive presentation from the data system, wherein the at least one update includes information selected from a group comprising new procedures, pharmaceuticals, statistics, and modifications to the at least one interactive presentation; and updating the at least one interactive presentation.

23. The remote device of claim 21, wherein the remote device is further capable of:

recording at least one personal marker of the patient comprising at least one biological marker selected from a group comprising pulse rates, breath rates, blood pressure, fingerprints, toe prints, footprints, corneal scans, and retinal scans;

encrypting the at least one recorded patient education session for transmission; and transmitting at least one recorded patient education session to a data system, wherein transmitting is performed over a medium selected from a group comprising bidirectional networks, wireless networks, and the Internet, wherein the at least one recorded patient education session includes the at least one interactive presentation, the at least one summary question, the recorded patient response, the recorded inquiry, the recorded visual images, a recorded personal marker of the patient, and the recorded electronic signature.

24. The remote device of claim 21, wherein determining patient comprehension comprises:

determining at least one score for at least one portion of the at least one interactive presentation using the recorded patient responses;

determining a status of the at least one score using a specified threshold;

when the at least one score is below the specified threshold, performing at least one action selected from a group comprising repeating the at least one interactive presentation, repeating at least one portion of the at least one interactive presentation, presenting information to supplement the at least one interactive presentation, readministering the at least one summary question, administering at least one additional summary question, and terminating the at least one interactive presentation.

25. The remote device of claim 21, further capable of correlating the at least one interactive presentation with at least one of the recorded visual images of the patient observing the at least one interactive presentation, the recorded patient responses, and the recorded at least one inquiry, wherein the correlation allows for simultaneous observation during presentation of a visual record of a patient education session.

26. The remote device of claim 21, wherein the at least one display comprises touch-sensitive screen through which the patient may enter information.

27. The remote device of claim 21, wherein the recording visual images is performed by a visual image capture device selected from a group comprising a digital camera, a digital video camera, and a video camera.

28. The remote device of claim 21, further capable of replaying at least one recorded patient education session, wherein the replay is correlated with the corresponding at least one interactive presentation, the recorded patient response, the recorded at least one inquiry, the recorded visual images, and the recorded informed consent.

29. A data system for obtaining informed patient consent, comprising at least one processor and at least one memory device, the data system capable of:

transmitting at least one interactive presentation to at least one remote device;

receiving and archiving at least one recorded patient education session from the at least one remote device, wherein the at least one recorded patient education session includes recorded visual images of a patient observing at least one interactive presentation and a recorded informed patient consent;

transmitting at least one interactive presentation update to the at least one remote device, the at least one interactive presentation update including information selected from a group comprising new procedures, pharmaceuticals, statistics, and modifications.

30. The data system of claim 29, wherein the at least one recorded patient education session further comprises the at least one interactive presentation, at least one summary question, a patient response to the at least one summary question, at least one inquiry of the patient, at least one biological marker of the patient, and a recorded electronic signature.

31. The data system of claim 29, wherein archiving comprises storing the at least one patient education session on an optical disk storage media.

32. The data system of claim 29, wherein the data system is further capable of transmitting at least one update to the at least one interactive presentation, wherein the at least one update is encrypted, wherein the at least one update includes information selected from a group comprising new procedures, pharmaceuticals, statistics, and modifications to the at least one interactive presentation.

33. The data system of claim 29, wherein the data system is further capable of correlating the at least one interactive presentation with at least one of the recorded visual images of the patient observing the at least one interactive presentation, the recorded patient responses, and the recorded at least one inquiry, wherein the correlation allows for simultaneous observation during presentation of a visual record of a patient education session.

34. A computer readable medium containing executable instructions which, when executed in a processing system, causes the system to obtain informed patient consent, the informed patient consent comprising:

providing at least one interactive presentation on a medical procedure;

recording patient response to at least one summary question of the at least one interactive presentation;

recording at least one inquiry of the patient during the at least one interactive presentation;

recording visual images of the patient observing the at least one interactive presentation;

determining patient comprehension using the patient response; and recording an informed consent including an electronic signature of the patient.

35. The computer readable medium of claim 34, wherein the informed patient consent further comprises:

transmitting at least one recorded patient education session to a data system, wherein the at least one recorded patient education session includes the at least one interactive presentation, the at least one summary question, the recorded patient response, the recorded inquiry, the recorded visual images, the recorded personal marker, and the recorded electronic signature;

receiving the at least one recorded patient education session; and archiving the at least one recorded patient education session, wherein archiving comprises storing the at least one patient education session on an optical disk storage media.

36. The computer readable medium of claim 35, wherein the informed patient consent further comprises encrypting the at least one recorded patient education session for transmission, wherein transmitting and receiving are performed over a medium selected from a group comprising bidirectional networks, wireless networks, and the Internet.

37. The computer readable medium of claim 34, wherein the informed patient consent further comprises:

receiving a transmission including the at least one interactive presentation from a data system; and selecting the at least one interactive presentation to provide to the patient;

receiving at least one update to the at least one interactive presentation from the data system, wherein the at least one update includes information selected from a group comprising new procedures, pharmaceuticals, statistics, and modifications to the at least one interactive presentation; and updating the at least one interactive presentation.

38. The computer readable medium of claim 34, wherein the informed patient consent further comprises:

recording at least one personal marker of the patient, the at least one personal marker comprising at least one biological marker selected from a group comprising pulse rates, breath rates, blood pressure, fingerprints, toe prints, footprints, corneal scans, and retinal scans; and correlating the at least one interactive presentation with at least one of the recorded visual images of the patient observing the at least one interactive presentation, the recorded patient responses, and the recorded at least one inquiry, wherein the correlation allows for simultaneous observation during presentation of a visual record of a patient education session.

39. An electromagnetic medium containing executable instructions which, when executed in a processing system, causes the system to obtain informed patient consent, the informed patient consent comprising:

providing at least one interactive presentation on a medical procedure;

recording patient response to at least one summary question of the at least one interactive presentation;

recording at least one inquiry of the patient during the at least one interactive presentation;

recording visual images of the patient observing the at least one interactive presentation;

determining patient comprehension using the patient response; and recording an informed consent including an electronic signature of the patient.

40. The electromagnetic medium of claim 39, wherein the informed patient consent further comprises:

transmitting at least one recorded patient education session to a data system, wherein the at least one recorded patient education session includes the at least one interactive presentation, the at least one summary question, the recorded patient response, the recorded inquiry, the recorded visual images, the recorded personal marker, and the recorded electronic signature;

receiving the at least one recorded patient education session; and archiving the at least one recorded patient education session, wherein archiving comprises storing the at least one patient education session on an optical disk storage media.

41. The electromagnetic medium of claim 40, wherein the informed patient consent further comprises encrypting the at least one recorded patient education session for transmission, wherein transmitting and receiving are performed over a medium selected from a group comprising bidirectional networks, wireless networks, and the Internet.

42. The electromagnetic medium of claim 39, wherein the informed patient consent further comprises:

receiving a transmission including the at least one interactive presentation from a data system; and selecting the at least one interactive presentation to provide to the patient;

receiving at least one update to the at least one interactive presentation from the data system, wherein the at least one update includes information selected from a group comprising new procedures, pharmaceuticals, statistics, and modifications to the at least one interactive presentation; and updating the at least one interactive presentation.

43. The electromagnetic medium of claim 39, wherein the informed patient consent further comprises:

recording at least one personal marker of the patient, the at least one personal marker comprising at least one biological marker selected from a group comprising pulse rates, breath rates, blood pressure, fingerprints, toe prints, footprints, corneal scans, and retinal scans; and correlating the at least one interactive presentation with at least one of the recorded visual images of the patient observing the at least one interactive presentation, the recorded patient responses, and the recorded at least one inquiry, wherein the correlation allows for simultaneous observation during presentation of a visual record of a patient education session.

\* \* \* \* \*